(12) United States Patent
Stapleton

(10) Patent No.: US 7,843,488 B2
(45) Date of Patent: Nov. 30, 2010

(54) VISION THERMALIZATION FOR SIGHTLESS AND VISUALLY IMPAIRED

(76) Inventor: John J. Stapleton, 6 Caldwell Ct., E. Brunswick, NJ (US) 08816

( * ) Notice: Subject to any disclaimer, the term of this patent is extended or adjusted under 35 U.S.C. 154(b) by 1803 days.

(21) Appl. No.: 10/914,257

(22) Filed: Aug. 9, 2004

(65) Prior Publication Data

US 2006/0028545 A1    Feb. 9, 2006

(51) Int. Cl.
H04N 9/47    (2006.01)
(52) U.S. Cl. ....................................................... 348/62
(58) Field of Classification Search .............. 348/61–63
See application file for complete search history.

(56) References Cited

U.S. PATENT DOCUMENTS

| | | | | |
|---|---|---|---|---|
| 3,704,378 | A * | 11/1972 | Robb | 250/222.1 |
| 5,469,511 | A * | 11/1995 | Lewis et al. | 381/173 |
| 5,636,038 | A * | 6/1997 | Lynt et al. | 358/471 |
| 5,851,423 | A * | 12/1998 | Teng et al. | 252/299.1 |
| 6,057,909 | A * | 5/2000 | Yahav et al. | 356/5.04 |
| 6,471,354 | B1 * | 10/2002 | Cho | 351/233 |
| 6,580,448 | B1 * | 6/2003 | Stuttler | 348/46 |
| 6,590,573 | B1 * | 7/2003 | Geshwind | 345/419 |
| 6,913,075 | B1 * | 7/2005 | Knowles et al. | 165/185 |
| 7,308,314 | B2 * | 12/2007 | Havey et al. | 607/54 |

OTHER PUBLICATIONS

Jones, Lynette A & Berris, Michal; "The Psychophysics of Temperature Perception and Thermal-Interface Design"; 2002 IEEE, 10th Symp. on Haptic Interfaces for Virtual Envir. & Teleoperator Systs. (Haptics '02); 0-7695-1489-8/02.

* cited by examiner

Primary Examiner—David Czekaj
(74) Attorney, Agent, or Firm—Gottlieb, Rackman & Reisman, P.C.

(57) ABSTRACT

A Vision Thermalization, "VT" light-to-heat transducer, versatile video transformation system, via Biophysics Resonance of forehead cells with thin film transistors infrared "display" (1 k×0.0015 C×640×480 VGA) and alternative image processing methodology thereof to convert, for the sightless and visually impaired, light waves, or TV received signals or 2D/3D video camera signals into infrared patterns of sensible heat waves such as produced by the product of voltage and current in an active matrix of thin film transistors (AM-TFT), typically used with liquid crystal displays, in order to exploit the viper-like thermal vision sensibility of 10 parts/million (0.003 C/305K) and biophysics resonance of thermo regulating amino acids.

20 Claims, 14 Drawing Sheets

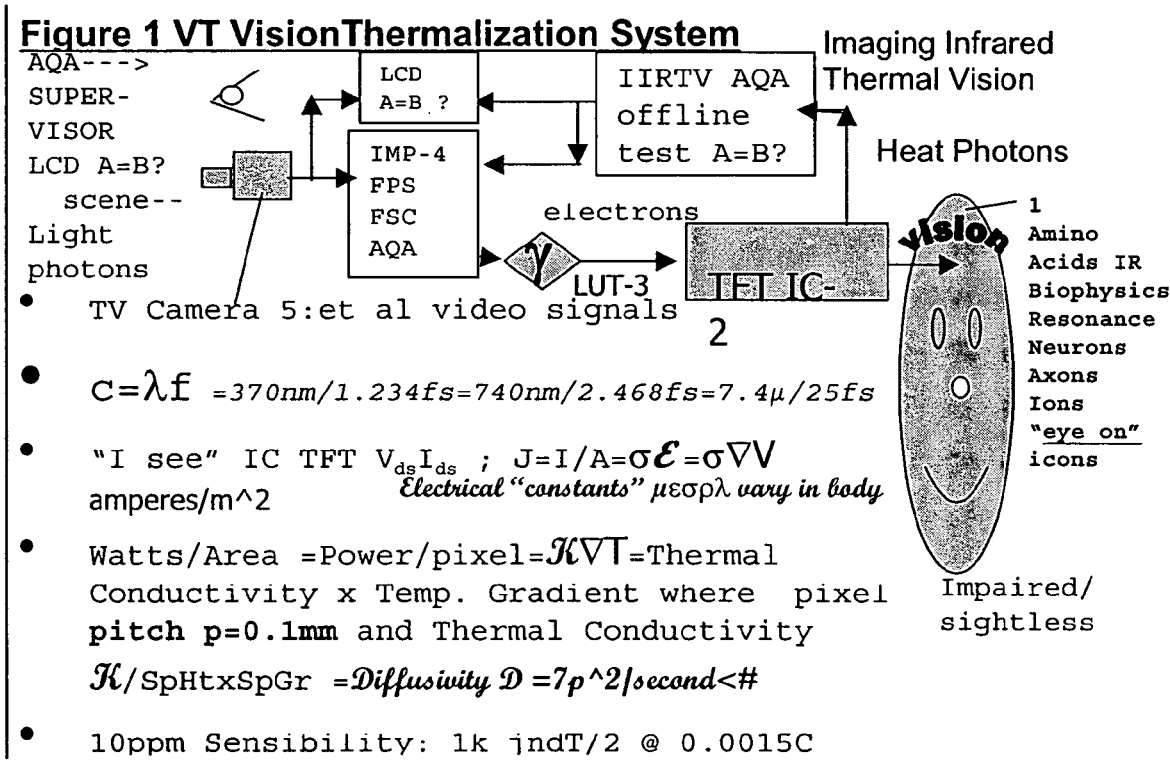

Fig. 2a VT 3D NEAR FLIR Stereo TV for the Sightless
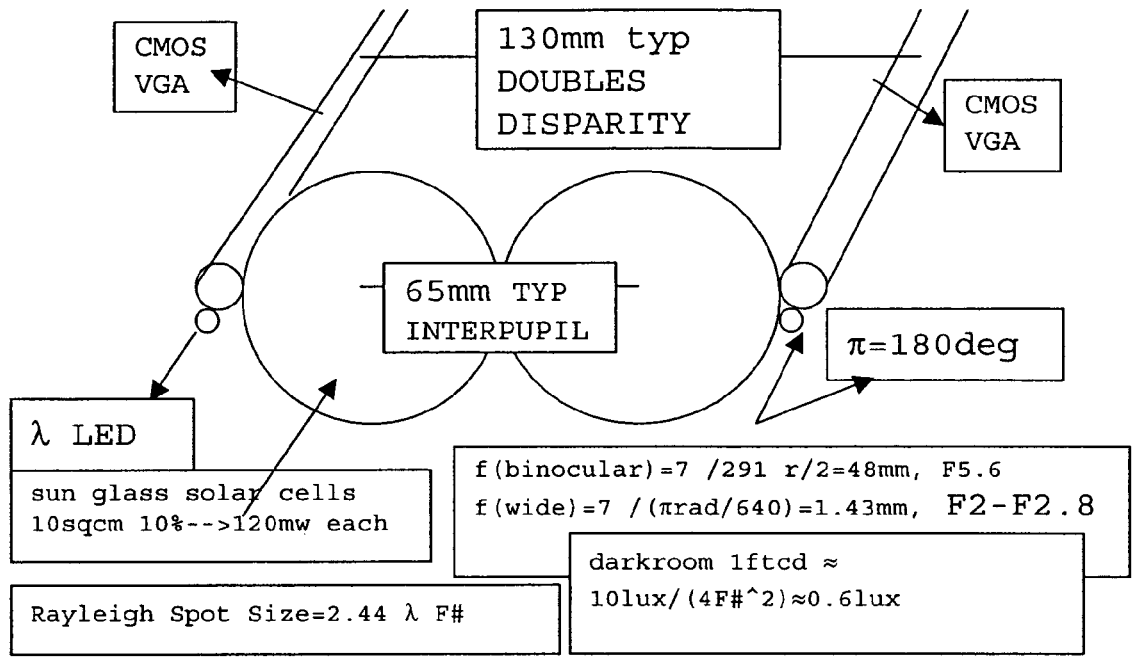
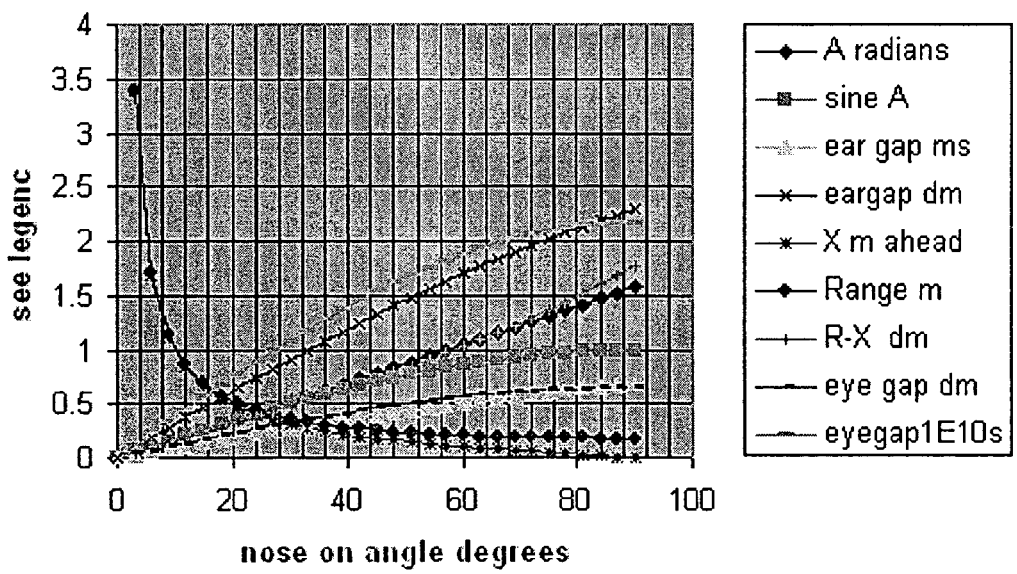

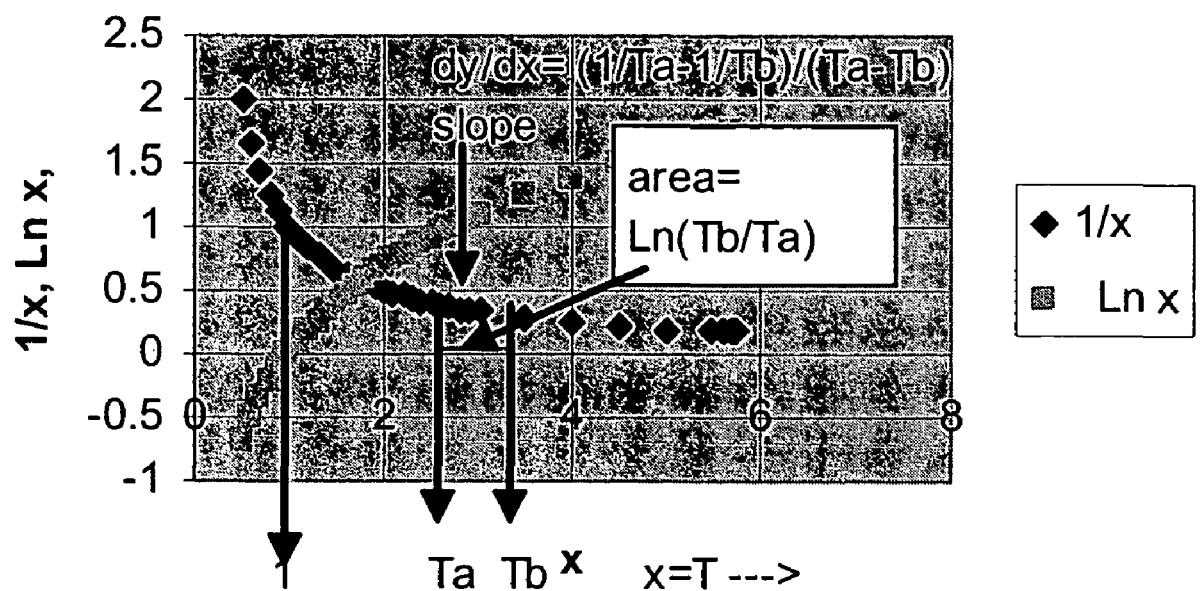
Fig. 2d 1/x, Ln x, LnT=integral 1/x, 1<x<T
Color Raitos: Judd's I/T <-->Weber Fechner Fig.3a OPT-->VT Simplified Model
100 micron voxel $(0.1mm)^3$
derivation from prior art tradeoffs

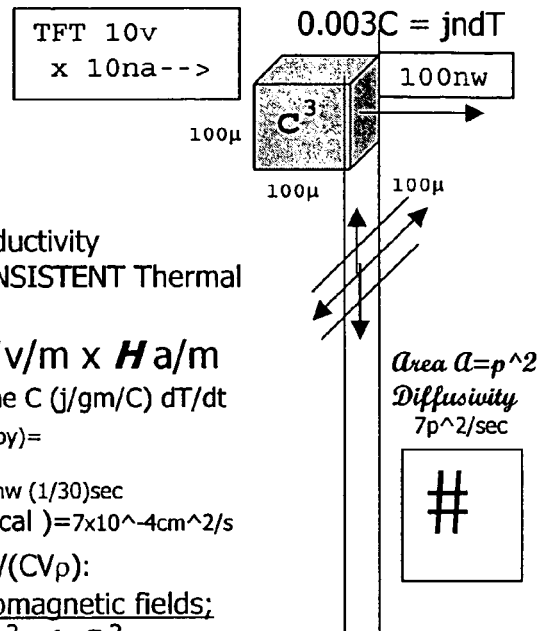

max mw/cm$^2$ =100nw/p$^2$; pitch p=0.1mm, Conductivity
$\mathcal{K}$=0.003w/cm$^2$/C/cm =100nw/p$^2$/0.003C/p CONSISTENT Thermal
R=1/Kp=0.003C/100nw $\mathcal{K}\nabla T$=power/area=W = $\sigma T^4$ =$\Pi$= Ev/m x Ha/m
$\mathcal{K}a\nabla T$=Watts=dQ/dt=massCdT/dt=densityxvolume C (j/gm/C) dT/dt
dQ(heat energy)=mass dT C(sp.heat)= T dS(entropy)=
=(10$^{-2}$ cm)^3xgm/cc x0.003C x cal/gm/Cx4.2j/cal=12.6nj
12.6nj=12.6nwatt sec =126nw (0.1sec)=90nw (0.14sec)=378 nw (1/30)sec
*Diffusivity* $D$=*3mw/cmC/* (gm/cc x cal/gm/C x 4.2j/cal )=7x10^-4cm^2/s
$D\nabla^2 T$ =(p^2/0.14sec)$\nabla^2 T$ =$\delta T/\delta t$= $\mathcal{K}a\nabla T/(CV\rho)$:
NOTE 1$^{ST}$ time derivative, not 2$^{nd}$ as with electromagnetic fields:
$\delta^2 \mathbf{E}/\delta t^2/\nabla^2 \mathbf{E} = \delta^2 \mathbf{H}/\delta t^2/\nabla^2 \mathbf{H} = 1/\sqrt{\mu\varepsilon} = c^2 = (\lambda f)^2 =$
=energy/mass=(space/time)^2
$\rho\varepsilon\equiv\varepsilon/\sigma$=RC=$\tau$=1/$\omega$=30usec; C/$a$=1ufd/cm^2=100pf/p^2; J=$\sigma$
=I/$a$

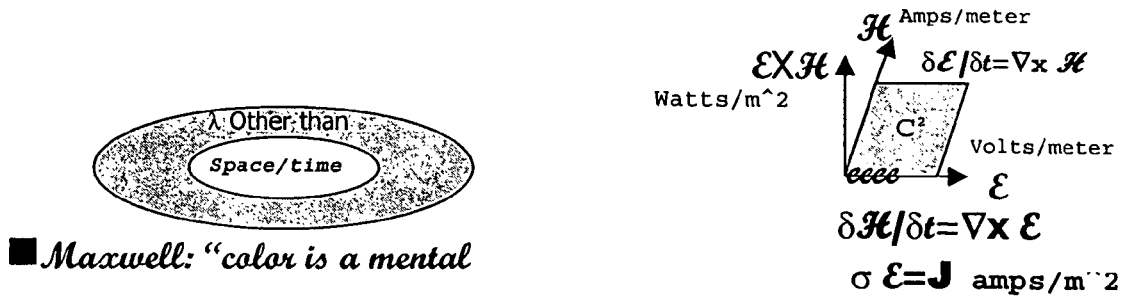

■ *Maxwell: "color is a mental*

$$c^2 = (\lambda f)^2 = 1/\mu\varepsilon = \text{1/(permeability x permittivity)}$$

$$c^2 \nabla^2 \mathcal{E} = \delta^2 \mathcal{E}/\delta t^2 \text{ and } c^2 \nabla^2 \mathcal{H} = \delta^2 \mathcal{H}/\delta t^2$$

$\mathcal{E}/\mathcal{H} = \sqrt{(\mu/\varepsilon)} = Z = $ *Impedance*

Color is defined as those aspects of visible light other than spatial and temporal inhomogeneties.

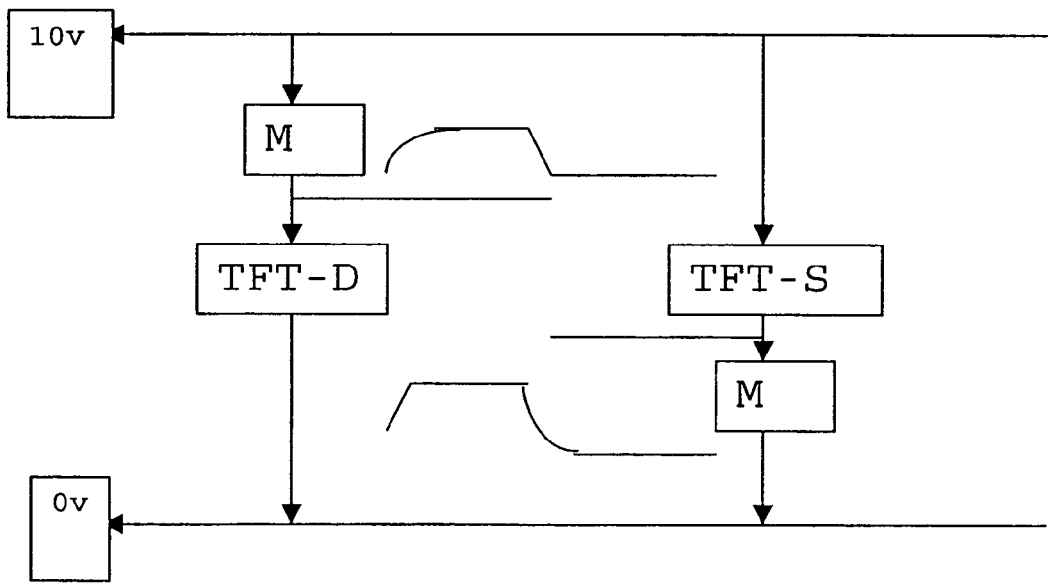

Fig. 3b after Dr. T.P. Brody, inventor of Active Matrix TFT displays c. 1975

Fig. 3c "TOTEM POLE PAIR" TFT J&B Stapleton's flexible display patents

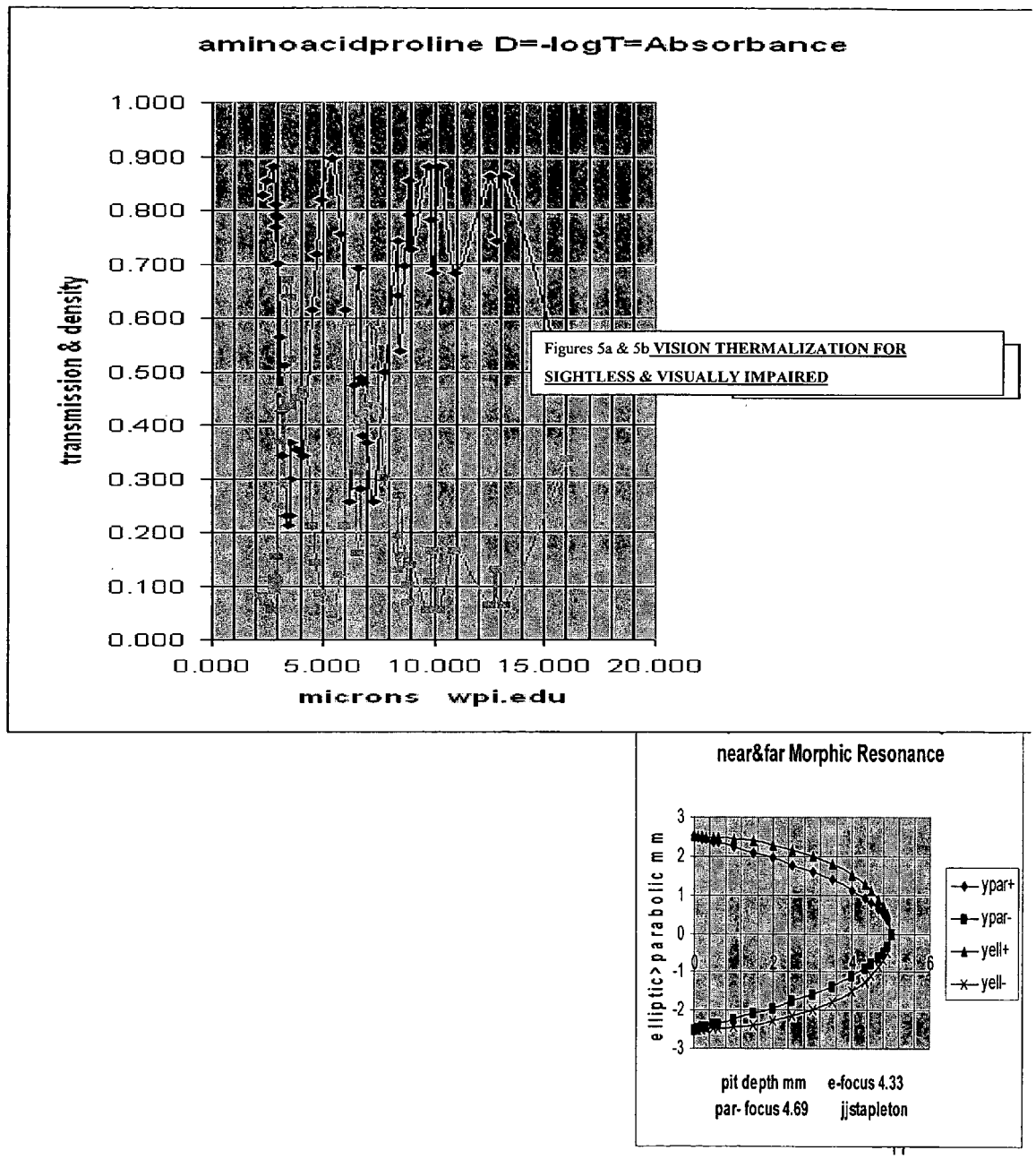

Figures 6a,b,c,d IR data
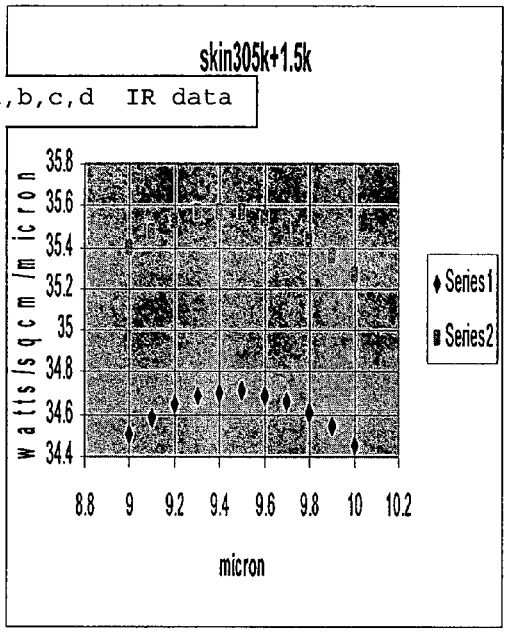
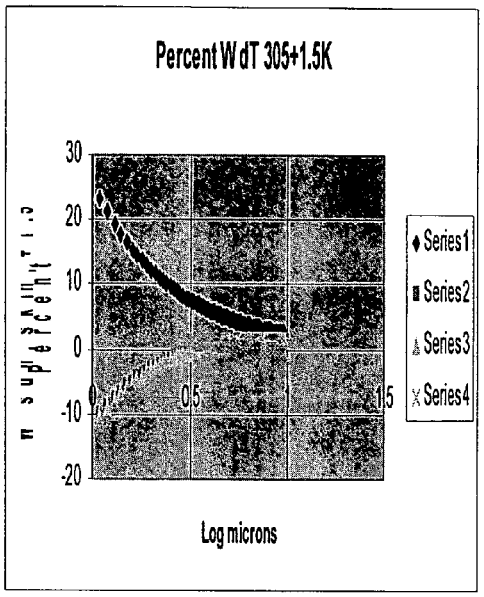
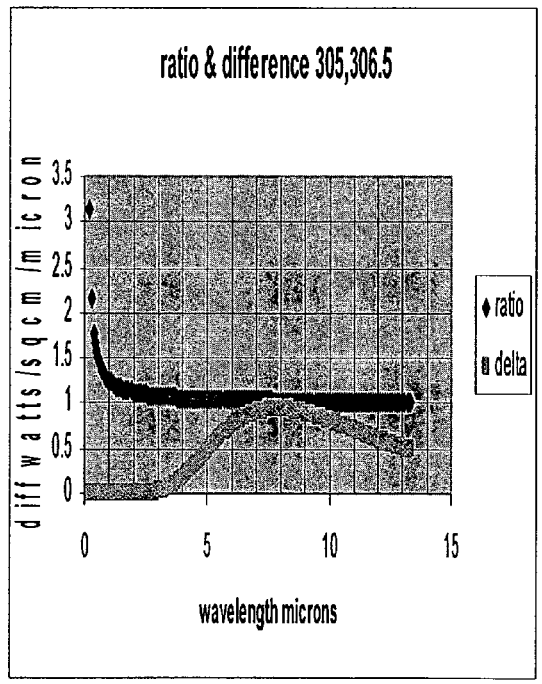
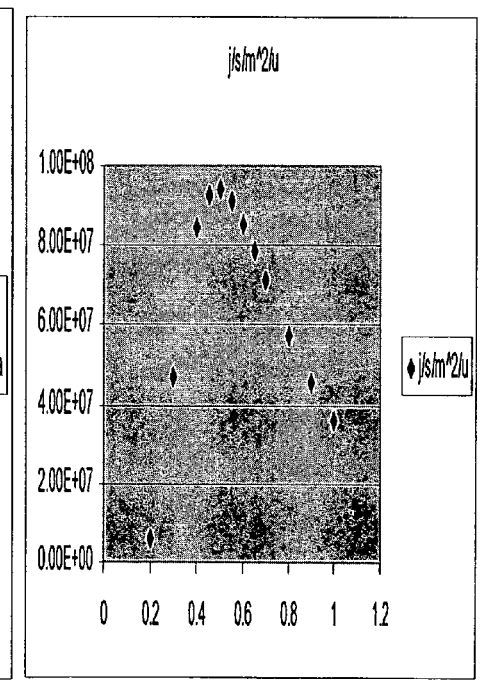

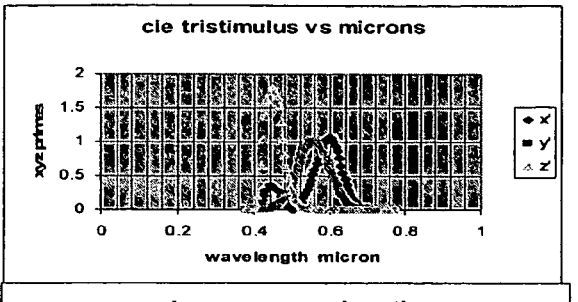
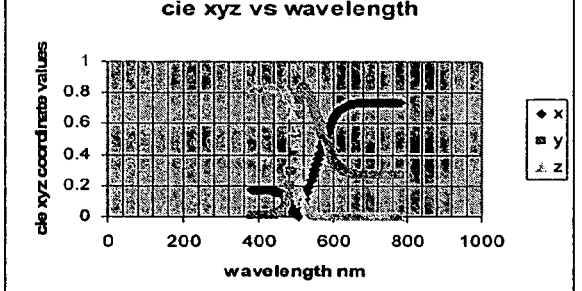
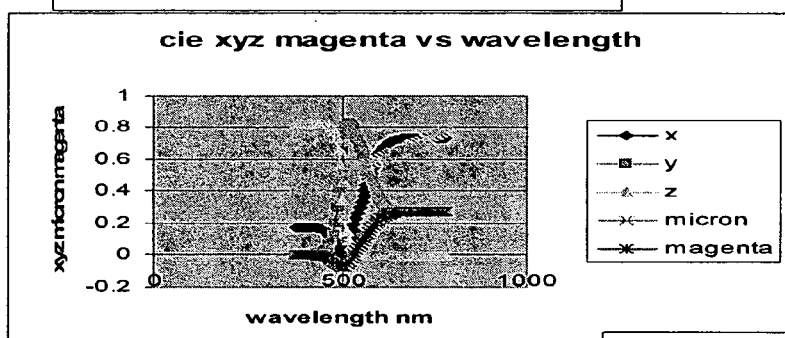
Figures 7a,b,c,d,e vision response data VT mimics via IR biophysics resonance of amino acids like Nathans measured in retina visible spectrum
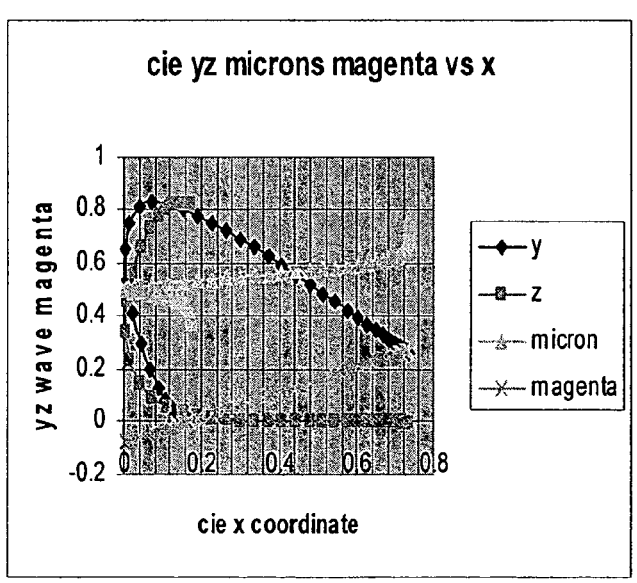
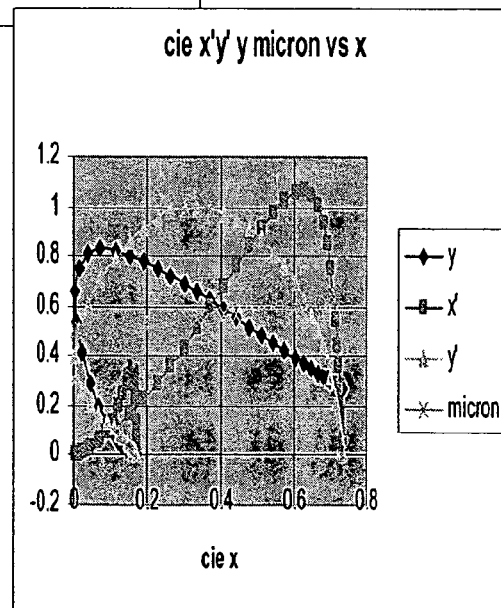

Fig. 8 MIT L.Jones thermoreceptor Info on internet + interpolations & graphics

| degC/s& sqmm | degC rise | deg C/ min | sqcm | 10mw/cm2 | 10*mw | Kelvin deg |
|---|---|---|---|---|---|---|
| 0.01 | 3 | 0.6 | | 19.62213 | | 308.16 |
| 100 | 2.4 | | 1 | 15.65154 | 15.65154 | 307.56 |
| 1 | 2.4 | | 1 | 15.65154 | 15.65154 | 307.56 |
| 0.025 | 1.75 | 1.5 | | 11.37622 | 15.93171 | 306.91 |
| 200 | 1.25 | | 2 | 8.10594 | 16.21188 | 306.41 |
| 2 | 1.25 | | 2 | 8.10594 | 16.21188 | 306.41 |
| 300 | 0.75 | | 3 | 4.851632 | 14.5549 | 305.91 |
| 3 | 0.75 | | 3 | 4.851632 | 14.5549 | 305.91 |
| 400 | 0.6 | | 4 | 3.878446 | 15.51378 | 305.76 |
| 4 | 0.6 | | 4 | 3.878446 | 15.51378 | 305.76 |
| 0.05 | 0.5 | 3 | | 3.230451 | 15.50616 | 305.66 |
| 600 | 0.4 | | 6 | 2.583091 | 15.49854 | 305.56 |
| 6 | 0.4 | | 6 | 2.583091 | 15.49854 | 305.56 |
| 0.1 | 0.3 | 6 | | 1.936366 | 17.42872 | 305.46 |
| 12 | 0.25 | | 12 | 1.613242 | 19.3589 | 305.41 |
| 1200 | 0.2 | | 12 | 1.290277 | 15.48332 | 305.36 |
| 0.3 | 0.1 | 18 | | 0.644821 | | 305.26 |
| | 0 | | | 0 | 0 | 305.16 |

L.Jones:

"prodigious capacity for adaptation"

(=definition of visibility)

Weber factor discriminability 2% resolve 0.02-0.05C transient area summation refers to constant product of dT and area

[JJS Notes Regulation at Constant Power despite forced dT Temp Change]

thermoreceptors are NOT thermometers warm 50-70/sqcm conduct6 1-2m/s cold 30x warm conduct 10-20 m/s others argue thermoreceptors are NOT submodality of touch elsewhere cold drop 10 to 0 firings/sec between 30-42C as warm rise 0 to 10 then peak at 47C, 38 firings/sec body heat cap 3.49 vs 4.18 water kj/kg/C 1.8sqmeter skin area = 1000 x retina and comparable million axons 1250 kg/cubic meter= 1.25 g/cc vs 1.0 used for water Even the negative feedback from MIT papers seems small given the expert opinion of L.Jones that the thermoreceptor/thermal regulation has "prodigious capacity for adaptation."

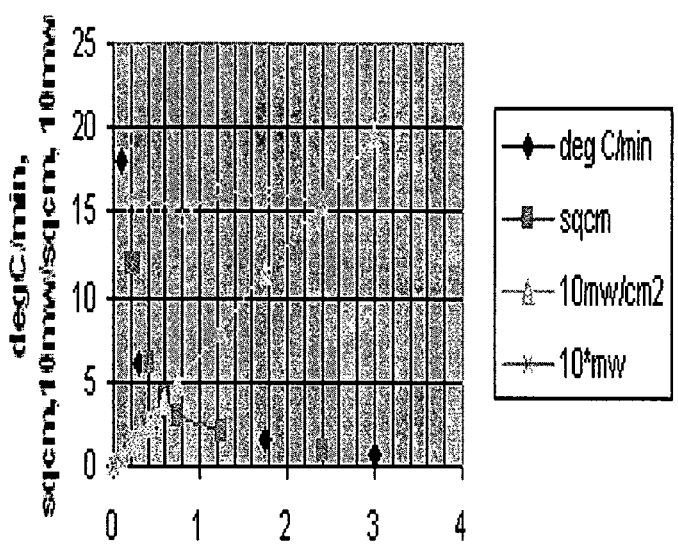

FIG. 8A

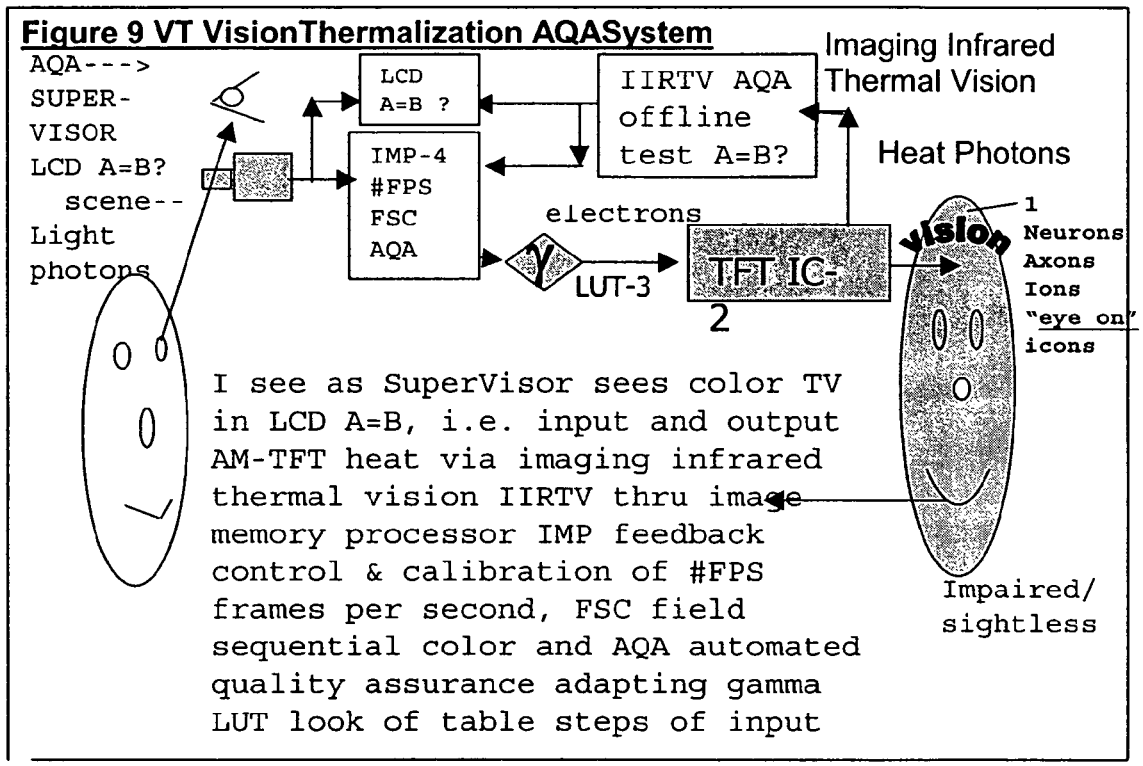
VISION THERMALIZATION FOR SIGHTLESS & VISUALLY IMPAIRED
Pending Patent  Application 030801 JJ Stapleton, Pte.
CONFIDENTIAL, PROPRIETARY & COMPETITION SENSITIVE INFORMATION

VISION THERMALIZATION FOR SIGHTLESS AND VISUALLY IMPAIRED

FIELD OF THE INVENTION

The present Vision Thermalization (VT hereinafter) invention is directed towards light to heat versatile video transformation system and alternative image processing methodology thereof to convert for the sightless and visually impaired light waves, TV received signals or 2D/3D video camera signals for the purpose of making infrared patterns of heat waves such as produced[1] by the product of voltage and current in an active matrix of thin film transistors (AM-TFT) typically used with liquid crystal displays thereby exploiting the human forehead's viper-like thermal vision sensibility[2] of 10 parts/million (0.003 C/305K) and biophysics resonance[3] with the infrared quantum vibrations or rotations of inhibitor and excitor amino acids[4] communicating the thermoregulator error signals and control feedback[5] analogous to normal sight.

[1] a Hughes patent teaches how video can be projected as IR image
[2] sc am
[3] biophysics resonance is defined herein as
[4] aa
[5] feedback

BACKGROUND OF THE INVENTION

Present medical science and technology have not yet quite perfected retina implants which to date provide limited restoration of sight for a limited number of the sightless and visually impaired, due to various eye diseases, despite all the good intentions in the world, altruism, philanthropy etc. But now with VT alternative vision, traceable to viper-like-vision back hundreds of millions of years of evolution,[6] the most recent discoveries and background development enrich the understanding and credibility of VT. Why now and not before? Potentially producing millions of new viewers of TV "eye candy" and advertisements and a lucrative commercial market of consumers, advertisers and investors with foresight can produce vision for the sightless. The effective expansion of TV for millions of new viewers is estimated to worth about $5,000 per cable TV home so even at Intel prices of billion dollars per acre, the VT ballpark price of $768/64×48 mm should be affordable to all in need.

[6]

The VT capitalizes on the billions of dollars[7] spent in developing its sensors and active matrix thin film transistors (AM-TFT) for the LCD but without the liquid crystal here. In a word VT electronics simply reverses thermal vision and Omnispectravision 3 IR bands transformed to visible RGB. VT, with or without color or 3D will be a very helpful, but inexpensive product to produce vision of invisible observables. It could be the immediate interim device until the implant nanotechnology surgeries are perfected.

[7] SID, standord resourses,

Color VT theory is byproduct of Research & Development (R&D) of The Total Image Process©[8] far beyond original academic quest for color closure resulting in U.S. Pat. Nos. 6,489,997 6,124,893 5,832,140 5,803,082 5,537,483 5,019,807 4,418,359 4,361,785 4,343,020 4,338,627 4,304,491.

© The Total Image Process is copyright and service mark of John J. Stapleton, Pte. and title of PhD
[8] Total Image Process Process is copyright, service mark of John J. Stapleton, title of PhD R&D VT is fortuitous outgrowth of Newton & Nathans (JHU) Quantum Visual Vibrations[9] and The Total Image Process PhD Research (SUNJ). Vision thermalization for the sightless relies on natural energy-efficient coupling by biophysics resonance and mature video technology. VT invention does not claim, presume, purport or promise "sight for the blind," but proposes to restore the innate thermal vision via forehead and analogous, inscrutable pathways of Braille touch signals thru the visual cortex.

[9] nathans

Resulting from quest for comprehensive color closure of extra-spectral magenta beyond the rainbow, in order to optimize vision of invisible observables for medical and military displays, as first demonstrated with 3 infrared wavelengths within the 3-5 micron band, around the 4.2 micron (2381 cm^−1) absorption of carbon dioxide, the vision thermalization design approach again mimics nature or restores the innate viper-like-vision from which human vision evolved hundreds of millions of years ago.

VT perturbs the error signaling in the thermoreceptors feedback control system to cool or warm forehead cells.

That new IR hue clue "from the pits" of vipers became a more powerful discriminant of blackbody radiations than color temperatures via remote IR resonance through supposedly "opaque" atmosphere[10] with the carbon dioxide quantum vibrations at 4.2 microns from missile threats contrasting them from natural clutter and noise, not substantially far from the 3.5 and 7-11 micron amino acids absorptions[11] of VT signalization for visualization via biophysics resonance.

[10] RCA EO Handbook, Lowtran program
[11] aa abs

Restoring the innate viper-like vision in the sightless seemed less daunting because vision is in the mind whereas sight is in the eye, easily mimicked by a TV camera whose signals had been transformed to various alternative means of stimulation for crude verisimilitude of sight signals. VT was never intended to be "disruptive" to the retina implant research and others medical marvels in development. Obviously VT profits may become disruptive to the status quo and marketplace of white canes, seeing-eye-dogs, audio descriptors of TV, and Braille, whose tactile signals have reportedly been traced through the visual cortex. So should VT IR radiation and conduction signals, responsive to pen-size 3D binocular color TV cameras on both sides of eye-glass frames powered by solar cells in place of usual lenses.

While not itself patentable, the recent discovery of biophysics resonance, is the enabling principle of viper-like-vision thermalization (VT) of 3D binocular color TV camera signals for the sightless, which seems analogous to the findings reported by Dr. J. Nathans, MD, PhD, (ScAm 1989) now at John Hopkins University. As previously discovered and reported (J J Stapleton "The Action of Light" SID NYC), the photon transit times to the depth of hue within the retina, are equal to, and thus in resonance with Nathans' measured periods of the quantum oscillations of certain amino acids comprising the pigment proteins. Together this forms the radical (root) basis for proposing vision for the sightless.

Specifically different from the color ratio processing of infrared (IR) and visible images by the pit-vipers (ScAm c. 1980) dual sensor pairs, VT exploits the same sensibility of 10 parts per million (<0.003K/300K) of the dual (cold/warm) thermoreceptors in the human forehead skin described below. They can be made to mimic the photopic/scotopic ratiometric retinal responses of human color vision by exploiting IR quantum vibrations/rotations of specific amino acids responding in biophysics resonance with a heat "display," instead of light, from a conformable, bandaid-size active matrix of thin film transistors (AM-TFT), already perfected by billions of dollars invested in LCD liquid crystal displays and solid state imagers (CCD & CMOS).

The eye-brain physiology and the nervous system[12] forms human nature's own "information technology" and innate telecommunications[13] that convey command and control information from one part of the body to another A break through clue came from reports that the tactile signals from Braille were traced through the visual cortex[14], as fast as 400 words/minute[15] which is above average reading rates for the sighted. While an amount of versatility in energy-efficient resonance has been provided by U.S. Pat. Nos. 4,361,785, 6,489,997, 6,124,893, the disclosure of which is incorporated herein, it is desirable to exploit biophysics resonance of infrared quantum vibrations/rotations of certain inhibitor and excitor amino acids communicating the thermoregulator homeostasis[16] error signals and control feedback analogous to normal retina transducers but with the infrared radiation frequencies and heat conduction produced by the VT AM-TFT rather than by visible light.

[12]CNS Nobel Prize
[13]Prof. Daut classes Rutgers SUNJ
[14]NYTimes Braille signal
[15]400 wpm
[16]homeostasis In the past, there have been other helpful devices to assist the blind such as the white walking cane, seeing eye dogs, and numerous others, including audio and coarse thermal stimuli on the back of the blind, and recently audio descriptors of TV pictures. The latter has peaked commercial interest beyond the altruism of 4 solicitors seeking sight for the blind.

While the present invention is not directed towards improving video components per se, it is ironic that the fault-tolerant totem pole pair AM-TFT taught in U.S. Pat. No. 5,019,807 to enable the flexible large screen "Windowshade TV"[17] to roll up out of sight can now empower the out of sight (sightless) people to "see" TV and normal visible objects heretofore unobservable or illegible through a conformable, bandaid size IR "display" in resonance with the forehead cells IR quantum vibrations. This is being accomplished in three stages, first in monochrome, then with color vision associated with taste of color foods and with 3D binocular stereo vision generated by pen-size video cameras (CMOS/CCD) along the sides of sunglasses where the lenses are replaced with solar cells to power the sensor, display, processor and optional laser to range-gate and photogate depth perception even in the dark.

[17]TV Digest Sep. 13, 1983

In this last regard, sensing range or distance better than with the white cane or seeing eye door distance seems critical for success, whereas "color" may turn out to be an expendable luxury even though the viper vision is two color (visible and IR). Low light, night (light or thermal) vision devices developed for military operations have been provided for a fraction of the visually impaired such as by ITT Night Vision.

As to the first objective of vision for the sightless, once produced properly, it allows the second color objective and third 3D binocular stereo vision to be met. The revolutionary idea is actually a reverse evolution from viper vision to human vision. The optimum quality of resolution potentially higher then the initial, commonplace VGA 640×480 is desirable but there is limited data and conflicting data (<1 line/mm to 70 lines/mm) on the thermoregulators just noticeable thermal gradient resolution (jndT/dx) which this invention will determine to optimize the design features.

Fortunately for useful depth perception, dynamic range, field sequential color temperatures, and for acceptable blackbody radiation levels, the CMOS/CCD sensors and AM-TFT "display" perfected by billions of dollars invested in them, are compatible with significantly higher refresh rates than standard TV 30 frames/second so as to exploit diffusion dynamics and diffusivity less than 8 nearest neighbors in one second.

SUMMARY OF THE INVENTION OBJECTIVES

It is an object of the present invention to provide for the sightless and visually impaired the fullest fidelity, image integrity of normal vision within the biophysics resonance limits and affordable, cost effective constraints It is a further object to provide externally image quality enhancements eg. adaptive nonlinear grayscale "gamma" correction in look up table LUT.

It is also an object to provide buffer storage for variable refreshing rates of images to optimize the peak and average power dissipation within the 1 milliwatt per square centimeter maximum allowable radiation (FCC/FDA) In this regard, briefly, the present invention provides 1024 steps of 0.0015 C or maximum temperature rise of 1.5 C i.e. 1 mw/cm^2 difference between 306.5 and 305 C nominal skin temperature.

It is a further object to provide without objectionable aliasing or flicker remarkably higher resolution than is ordinarily expected by thermoreceptor cells in thermal equilibrium and by Nyquist sampling theorem and averaging circuits. In this regard, briefly, the present invention exploits diffusion and the edge-enhancer Laplacian operator mechanized as the difference of a pixel value and its nearest neighbors average in the image process electronics as well as in the ganglion cells and amino acid inhibitors and excitors.

It is also an object to provide enabling technology for the sightless to "see" PC displays, internet, palm pilots etc. thereby vastly expanding the benefits of the American Disability Act (ADA).

It is a yet further objective of versatility in expandability up to the fullest possible sensation of realism such as 65K×65K pixels of MPEG or UHD ultra high definition Intelepresence.

It is a secondary objective of VT sought by US DoD and Homeland Security to empower and optimize the fusion of multispectral sensors for the battlefield visually impaired by natural and enemy obscurants in the "fog of war." In this regard an exotic objective and extension of VT IC IR "display" is to in fact display the biophysics resonance in near IR with the prefrontal cortex and ultimately remote sense a liar or security threats such as at airports along the lines of minereader research at UPENN[18].

[18]UPENN

It is a commerce objective of VT to empower the sightless to see TV so that advertisers will enjoy and support millions of new viewers and completion of the ultimate object of the invention to provide a progressive synergism of the multiple functions of present assistive devices.

Last but not least, it is reliability objective of VT to incorporate feedback command and control for Laboratory and factory testing such that a SuperVisor also sees comparable color TV in LCD A=B, i.e. input and output AM-TFT heat via imaging infrared thermal vision IIRTV thru image memory processor IMP feedback control & calibration of #FPS frames per second, FSC field sequential color and AQA automated quality assurance adapting gamma LUT look of table steps of input light to optimum heat levels out.

The present invention provides for the foregoing objectives by providing for a means to transform light waves to heat waves of IR images and receive, decode and encode remote or direct video while substantially exploiting the instantaneous dynamic range comparable to normal vision and 10 parts/million temperature sensibility.

BRIEF DESCRIPTION OF THE DRAWINGS

Thus by the present invention its objects and advantages will be realized, the description of which should be taken in conjunction with the drawings wherein:

FIG. 1 is a general system level block diagram of the present invention showing how Vision Thermalization converts electromagnetic waves of light frequency f in discrete quantum of energy (E=hf) called photons to electrons then into a picture of heat photons whose change in momentum causes the radiation pressure equal to the differential energy density thus providing biophysics resonance with the thermo regulating amino acids' IR absorbing vibrations/rotations. How these IR waves and photons beget neurons, axons, action potential electrons, ions ("eye-ons"), icons ("eye-cons") or images in the brain of the sightless is beyond the scope of the invention but remains to be more fully explained below with VT feedback control data by collaborating medical specialists and molecular biologists.

[19]see psyiology, biophysics, biochemistry in bibliography
[20]Gray, Tortora
[21]warm&cold FIG. 5a illustrates by way of example typical IR absorbance and transmission of an amino acid proline which data closely resemble glycine and glutamine that known to be inhibitors and excitors respectively in the skin whole FIG. 5b exhibits the pit vipers thin film membrane eccentricity from VT R&D to explain how the infrared imaging is accomplished in viper vision in reported tests of far and near field fixation comparable to the human foveal fixation.

FIGS. 6a-6d graphical represent the pertinent IR relationships.

FIGS. 7a-7e show overlays of visual responses[22] for VT to mimic.

FIG. 8 interpolates between data points reported by MIT L. Jones.[23]

Figures 2C, 2D:
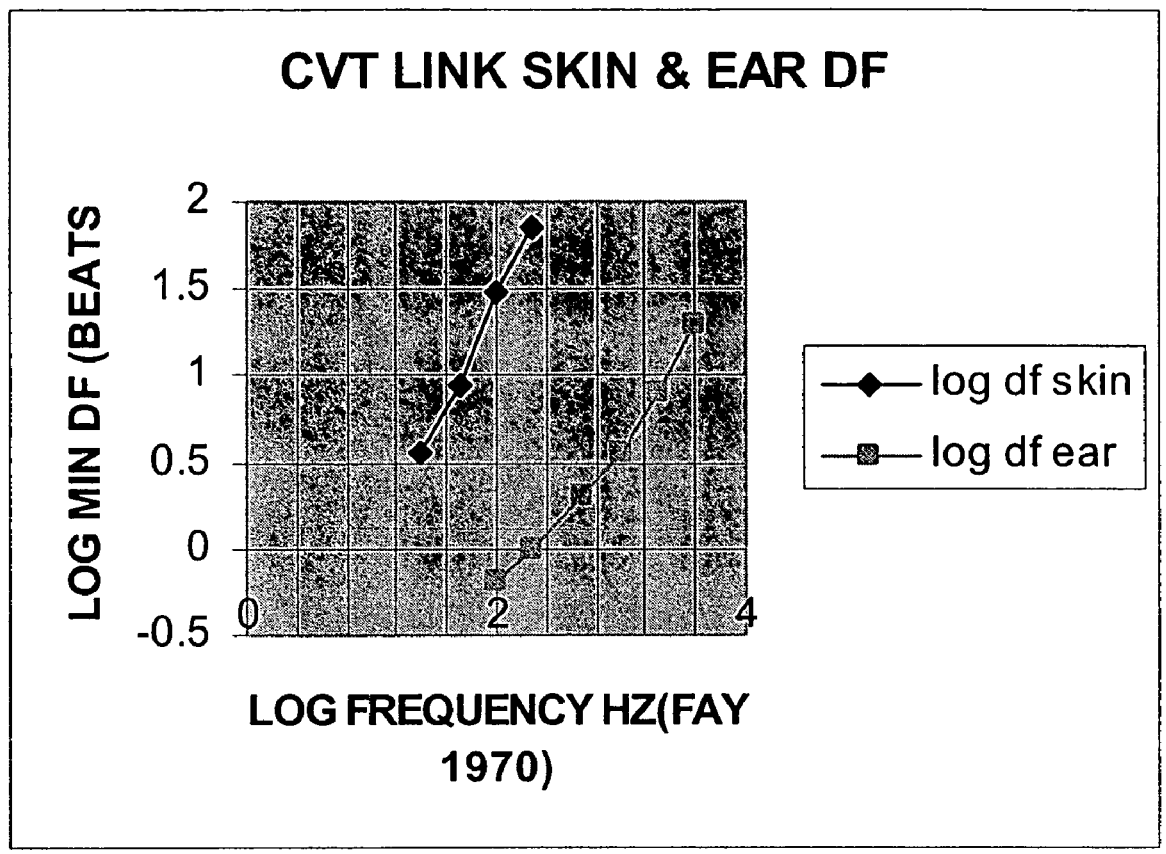
FIG. 2a illustrates the 3D Near FLIR stereo TV sensors for the sightless and FIG. 2b graphically shows stereo sight and sound capabilities, FIG. 2c plots Fay data of df v f for skin & ear, and FIG. 2d relates Judd's 1/Ta-1/Tb to Weber Fechner Ln T

[22]RCA EO Handbook, CRC
[23]Jones, L.

FIG. 9, details subsystem of Figure ! that incorporates offline and realtime feedback command and control for Laboratory and factory testing such that a SuperVisor also sees comparable to VT perceptions of user, color TV in LCD A=B, i.e. input video and output AM-TFT heat images.

DETAILED DESCRIPTION OF THE PREFERRED EMBODIMENTS

Nonlinear optimization dictates that one design such grossly nonlinear vision systems "backwards" starting with the last stage first[24], that is the eye-brain 1, then the display 2, image processor 3, sensor 4 then illuminator 5. Accordingly in FIG. 1, since signal flow generally goes left to right, the key items of the VT system are labeled 1 to 5 from right to left. How does the touch signal in brain from Braille get processed via the visual cortex? Should not the "grass roots" ganglion cells in the thin film display called the retina operate like those beneath the forehead skin[25] processing sensible heat signals rather than the retina photodetector signals?

[24]Operations Research
[25]ganglion cells

Humans vision normally is limited to less than one octave of the electromagnetic spectrum 370-740 nanometers (nm), centered about 555 nm where color discrimination is weakest because the peak daylight (photopic) response 683 Lumens/watt equals the twilight (scotopic) response. (Tilton) Vision thermalization is based on a radical hypothesis that vision may have been an evolutionary shift from infrared (IR) to visual quantum vibrations in amino acids complementary color reactions to vegetation coloration. About 300 years after Newton's prism split white light into a spectrum of rainbow colors, J. Nathans, MD, PhD at Stanford University (now at Johns Hopkins University) actually measured the visual vibrations Newton postulated[26] with his simplistic analogy that pitch is to sound as color is to light.

[26]Newton, I. Optiks, Dover, N.Y.

pitch/sound=color/light=vision thermalization/infrared vibrations

Early VT theory was based on the premise that one could exploit the brain's remarkable regulation of body temperature (hypothalamus thermostat[27]) that requires feedback control "error" signals to maintain the remarkable sensibility in the human tongue and forehead, as in pit vipers, namely a "just noticeable differential temperature" jndT or intrinsic NET noise equivalent temperature 0.001 C°-0.003 C°. This action is achieved by propagating nerve "action potentials" from the cell body to the axon terminal[28]. Because these measured action potentials vary from 0.7 kT to 3.8 kT above the random background thermal noise of kT=26 mv, that is 3.5 times below the −90 mv of the sodium-potassium pump, the signal to noise ratio and instantaneous IR dynamic range are expected to meet or exceed normal vision.

[27]thermostat
[28]cns

The cell membrane physiology applies to both nerve and muscle and it becomes depolarized (by 15-25 millivolts from about −90 millivolts)[29] as determined by the magnitude of action potential and membrane excitability. The nerves reported[30] conduction velocities increase nearly linearly with temperature at 5%/C° or 2.5 meters/second/C° from nominal 40-60 m/s over a large dynamic range of 29 to 38 C°. Hence the just noticeable differential temperature, jndT=0.003 C accelerates this velocity by 7.5 millimeters/second and 10 jndT's by 7.5 cm/s and 100 jndT's by 75 cm/s=30 inches/sec or 1 inch in 1/30 second TV frame time. 1000 jndT's are a bit too hot so 1000 jndT/2 will minimize quantizing noise, rise only 1.5 C and stay below the maximum allowed milliwatt/square centimeter. Although conduction velocities of muscle fibers is reportedly slower than nerve axons and estimated to be 4 or 5 m/s, one usually does not consider the forehead to be muscular. Note slower fibers are deep red from myoglobin content and the fast fibers tend to be whitish[31] as if mindful of the locus of blackbody color temperatures in CIE color space.

[29]nerve potentials
[30]velocity
[31]color

There is reason to believe that humans had viper-like thermal (infrared) vision of blackbody radiation eons before the human retina developed color cones and rods to adaptively respond by the biophysics resonance of the pigment proteins amino acids' quantum visual vibrations in sync with the difference in transit time (250-500 fs) of the photons to the depth of hue, due to the one percent variation of speed of light with wavelength. Most of the 20 amino acids have infrared absorption spectra around 3.5 and 7-12 microns[32] indicative of quantum vibrations with energy-efficient coupling at resonance with blackbody vibrations. Proteins[33] are natural polymers of biologic molecules made up of various combinations of amino acids that are building blocks linked by peptide bonds and thereby can catalyze reactions and regulate metabolic functions, such as precise body temperature, and perform other roles. The tuned sensitivities to one octave band of visual vibrations probably evolved as harmonic frequencies of caveman's very sensitive infrared (thermal) vision (0.003 C degree 10 parts/million) which sensitivity pit vipers still enjoy, as well as the human tongue and human forehead (ScAm c.1980).

[32]aa abs
[33]Devlin

For example[34], glycine (33% of amino acids in skin, 4% in hemoglobin) acts as an inhibitor (I) while glutamine (7% in skin, 6% in hemoglobin) acts as excitor (E) such that the ganglion cells in the skin reportedly effect the edge-enhancing Laplacian operator ("del-squared"$\nabla^2 T$) as in the retinal ganglion cells and digital image processing (Pratt) simply by the difference between a pixel and its 8 nearest neighbors average, such as

[34]aa glycine

| I | I | I | E | E | E |
|---|---|---|---|---|---|
| I | <u>E</u> | I | E | <u>I</u> | E |
| I | I | I | E | E | E |

Returning now to the methodology involved, for example the mean video value contrasting the center of a 3×3 # array is called the Laplacian operator that is employed in electronic imaging for edge enhancement as reportedly in the skin as well as in the visual cortex. The mean value yields the least "mean square error"[35] that is generally preferred because it is "tractable" i.e. easy to manipulate and consistent with the law of large numbers and large number of light and heat detectors in the eye and skin

[35]Paupolis

Turning now more particularly to the drawings, FIG. 1 shows the system functional blocks of the present invention in this regard including a feedback command and control subsystems for a Supervisor to compare what the sightless "sees". The TV type input signal may be received from the camera which light waves or DVD, VCR, broadcast antenna, cable TV or satellite or variety of video signals are transformed into an IR image by the heat of the AM-TFT. With NTSC standard 4.2 MHz video bandwidth the resolution is only 448×336 whereas the 6 MHz full channel capacity bandwidth permits the initial VT VGA resolution 640×480. The present inventions serves to overcome such limitations as will be discussed more fully. To further enhance perceived resolution beyond the controversial data on the skins thermoreceptors resolution, biophysics resonance of natural 3×3 arrays of cells in the forehead as shown with retinal resonance of 3×3 arrays with high definition Sparkle (U.S. Pat. Nos. 6,489,997, 6,124,893), VT is a visionary technology envisioned 70 years ago by Judd (NBS) and 50 years ago, in words of CBS Edward R. Murrow:

"This instrument can teach, it can illuminate; yes, and it can even inspire. But it can do so only to the extent that humans are determined to use it to those ends. Otherwise it is merely wires and lights in a box. There is a great, perhaps, decisive battle to be fought against ignorance, intolerance and indifference. This weapon of television could be useful . . ."[36]

[36]Murrow, E. R.

VT reverses TV display of military thermal (night) vision produced by infrared (IR) video cameras, the exploitation of which led to VT diffusion calculus below.

Incidentally as in same patent, a nominal user fee would offset broadcast or Copyright expenses if applicable, and be compensated by TV advertisers coupons or credit because even the sightless poor under ADA should be able to afford VT.

Turning now to the VT camera shown in FIG. 1, a functional detailed block diagram of 3D Near FLIR (forward looking infrared) stereo TV sensors for the sightless is shown in FIG. 2a. Because the perceived brightness is a linear response to density [=−Log(Relative Brightness)], the average of picture elements finer than arc minute resolution defined as 20/20 vision involves simple, scalar arithmetic. But the combination of picture elements chromaticity is a more complex, nonlinear vector process wherein mental attributes of hue and saturation (purity) are mental constructs traditionally represented by the vector angle and magnitude respectively, related to idealized Tristimulus[37] values and Photopic/Scotopic visual responses, conceivably evolved from warm/cold sense of cavemen.

[37]RCA EO Handbook, CRC

The flexible or preferably conformable fabric of new "bandaid" size TV screen created by the present invention, must be adaptive to the diverse surface contours of foreheads for most efficient coupling of the IR radiation and heat conduction. Gaps between a flat screen as used in present LCD production can be filled with appropriate thermal compound or soft mixture that does not diffuse the image. The picture fabric can be enhanced beyond VGA by the VVTD so that the high definition pictures SPARKLE in the full splendor of all 1920×1080 HDTV picture elements (pixels) woven together to unite the motionless interlaced or "progressive" noninterlaced fields, and decimated where there is motion in the image to minimize smear and temporal aliasing problems. Significantly higher and variable frame rates are anticipated so as to exploit the thermal diffusion formula whereby exposure thresholds are proportional to the square root of the IR pulse width or dwell time of the pixel peak power.

Support for the interpolation/decimation[38] and extension beyond Nyquist sampling limits can be found in Fogel, L. J., "A Note of the Sampling Theorem," IRE Trans. Info. Theory 1 Mar55 p47-48) and valid Taylor Series representation of any signal in terms of its time derivatives or Fourier Series in terms of sinewave frequency harmonics. The VT image processing effectiveness and operability is supported by the following publications: Optimum Signal Processing by (Prof)

Sophocles Orfanidis at Rutgers SUNJ, Discrete-Time Signal Processing by Oppenheim & Schafer, IEEE Special Issue on Digital Image Processing July 1972 and most recently Digital Television Fundamentals by Robin & Poulin and standards mentioned above as well as numerous papers and textbooks in biophysics and biochemistry to be appended.

[38]Papoulis, Pratt

Thermal vision and FLIR forward looking infrared before omnispectravision invention were monochrome with no hint from tint or else they used pseudo colors arbitrarily assigned to gray values of video, not bands of wavelengths. In essence the VT radical idea went back to the roots of viper vision, thermal vision devices and color ratios reported in pit vipers. VT R&D discovered viper means of IR imaging and simply reversed the process of thermal vision devices. Instead of transforming heat photons to electrons then light photons, Vision Thermalization converts light photons to electrons then a picture of heat photons.

Other night vision devices and LLL low light level TV for the military and some visually impaired people simply amplify the number of light photons. Upon review again of the ScAm article on pit vipers and further research, it turned out that the sensitivity of the human tongue and forehead is the same as the pit viper which is 0.003 C degrees or 10 parts per million. This is supported below by the explicit metric of color temperature "micro-reciprocal degree" (Judd JOSA 1933) and its implicit compliance with the Weber-Fechner law in psychophysics governing every sense.

The purpose of this thermal design formulation and analysis, as if the mind's visualization calculus, regulating color and skin temperature transients, is to re-present the derivation and novel exploitation of Fourier-Fick formulas in simple as possible "Pop Physics" because of the highly technical jargon of the many cross disciplines, either formulaphobic or formulaphillic, involved in the sophisticated physical and health sciences of vision, and lack of vision. VT is a visionary technology because again the integrated circuit IC has worked wonders for video="I see" in Latin.

With regard to the utility, specificity or producibility of 0.1 mm pitch p, data mining supports it in initial design, but not as optimum resolution VT experiments must determine. Very little has been found in extensive literature searches about the nature, anatomy or physiology of the thermoreceptors but what seems most reasonable is that earlier poor resolution, overcome by thermal diffusion calculations, are consistent with the fact that temperature changes gradually fade to thermal neutrality or equilibrium. Likewise steady-state normal vision is said to be inoperative without saccades and space/time samplings. Some believe the localized heating effect dq/dt=mC' dT/dt as explained thoroughly below, changes the ionic permeability for example the NaKCa "pump"[39] which induces the ion flow and action potential. In so far as the energy (heat) is distributed, the differential energy density at any interface equals the pressure, which typically describes the tactile or tactual sense of touch. It can not be repeated too often that the radiation pressure created by the VT AM-TFT picture of heat photons momentum are the formative causation of sympathetic IR vibrations, error signal perturbations, or biophysics resonance with absorption spectra of certain amino acids comprising the thermo regulating proteins, analogous to Newton/Nathan's (JHU) visual vibrations of pigment proteins in sync with photons transit times to the depth of hue, like tapping a pendulum or swing in resonance.

[39]NaK pump

Nevertheless optoelectronics, image processing, IR electro-optics do not teach us how to get the proper signals to the brain of the sightless from the forehead or tongue. Retina implants appear promising but so did AI artificial intelligence and fuzzy logic. The well understood VT heat image created from the TV may feel fuzzy or poorly resolved but it seems very promising after recent findings from studies of the latest textbooks in medical school. In fact the skin, for different reasons, appears to have the essential elements in the normal retina. Indeed there are rod-shaped and cone-shaped receptors in the skin and more remarkably ganglion cells which not only combine and compress the signals as in the retina but actually effect the Laplacian operator in that an exciter cell is surrounded by inhibitor cells as nearest neighbors and inhibitor cells are surrounded by exciter cells.[40] The same 3×3 # operator was exploited to enable HDTV to Sparkle with all 2 million dots and might triple the initial 10/mm to 30/mm, about half the finest found. But if the questionable 70/mm tactile resolution[41] or better proves useful then a proposed Intelepresence UHD ultra high definition 16,000×9,000 can match the eyes capacity and Intel challenge.

[40]# aa
[41]70/mm

Instead of TFT display devices for the VT, sensor chips with 10-25 micron pixels or RAM chips may be feasible. Or the back might be another backup, though not as sensitive. (ref. try c. 1972)

The morphology of the cone shaped and rod shaped photoreceptors, in the multilayer thin film display in the back of the eye called the retina, suggested among many in the past "morphic resonance" (Sheldrake) of their pigment proteins amino acids' quantum visual oscillations (Nathans) whose periods equal the difference in transit time of the photons to the depth of hue, (Stapleton SID NYC January 1997) due to 1% variation of speed of light with wavelength.

A detailed understanding of viper-like VT design is enhanced by FIG. 5b showing a cross section of a pit 5 mm in opening and in depth at approximately 8× magnification and the following novel explanation of pit viper's heretofore inexplicable IR imaging by the pit's adaptive membrane eccentricity to focus and fixate far and near fields of vision. VT R&D provided this first known means of adaptive far/near focusing that pit vipers probably employ by minor deformation of the pit membrane from a parabola (for reported far field >60 degrees) to semi-ellipse (measure and reported near field <5 degrees like human fovea). VT findings in all available books and internet items on snakes vision and infrared sensing did show how the pit vipers brain computes, commands and controls the thin membrane change in eccentricity e:

$$\text{far } 1.0 >= e => 0.866 \text{ near}$$

for far and near focus respectively. ScAm c1980 pit viper vision had not determined a means of focus essential for IR imaging.

Simply surmised, vipers sense heating microscopic voxels of water within the pits thin membranes. Biologists may think it is simply an autonomous, natural result of focusing so much collimated heat energy from afar such that the coefficient of thermal expansion enlarges and thereby reshapes the thin membrane from a parabola to ellipse. Their investigators tested and reported the pit viper, even blindfolded, can fixate, focus and "see" an IR image of a mouse 30 centimeters away wherein each voxel (3D pixel) whether continuous (analog) or discrete (as in human retina) the nonlinear absorption of differential energy densities are equal to the infrared radiation pressure.

This VT TFT heat generation, and black-body radiation pressures, responsive to a TV camera or other video signal, together with thermal and electric conductivity, diffusivity and permittivity parameters are the formative causation of communicating the sensation of heating a small voxel of water (a micro cubic centimeter) within the forehead skin as well as in the pit membrane, and in the differential energy density within the depth of hue within the 200 micron thin film display called the human retina (2.5 micron photodetectors).

Many wondered do pit vipers really and truly sense IR images or do they just measure an average temperature in the pits that appear somewhat like a blackbody cavity? The literature did not reveal how the IR image is formed, if at all. This viper's act of fixation and focus to 5 degree fovea region[42] is very similar to human vision. In sketching the pits said to be 5 millimeters deep with a 5 mm opening or aperture[43], it became apparent that their thin membrane could easily and quickly be deformed from a parabola to semi-ellipse or more accurately from a paraboloid, that concentrates collimated or distant rays to a focal point, whereas the ellipsoid has two focal points such that the sum of the distances to them from the membrane or surface is constant. Because any angle subtended by those distances to the two focal points is bisected by the normal, the angle of incidence thus equals the angle of reflection thereby suggesting biophysics resonance between one focus to the other and any point on the ellipse. Hence a cavity resonator model with such a deformable membrane seemed sufficient theory for the time being to agree with biologists who believed pit vipers have thermal vision and also see light. This resonator aspect of viper vision will be related later to VT color vision analogous to normal vision formative causation is the biophysics resonance of the quantum visual vibrations of certain amino acids comprising the pigment proteins with the radiation pressures within the depth of hue in the retina. Similarly IR radiation, conduction, and quantum vibrations in the quasi-retina forehead skin amino acids support this theory.

[42]viper 5 deg
[43]misplaced books on snakes—reference to be supplied,

In fact the incredible 10 parts/million sensitivity or NET noise equivalent temperature of 0.003K/300K seemed too good to be true for a remote sensing thermometer or integrator of blackbody radiation because the Stefan-Boltzman formula indicates $(300.003/300)^4 = 1.00004$ or 4 times larger or coarser than 1.00001. In fact some articles report the pit vipers NET is 0.001 C or 0.002 C. degrees, whereas the physics and electronics has not improved that drastically from 1973 when the instant inventor reduced Casper's Probeye NET from 1 C to 0.1 C and later to near 0.01 C with a demonstrated NEI noise equivalent irradiance on the order of 20 femtowatts per square centimeter. (Stapleton, Omnispectravision . . . SPIE & SID)

It seemed more likely that indeed the pit vipers perform at least one color ratio of red/infrared in the region of the electromagnetic spectrum where the spectral radiance of the light is falling and the near-IR is rapidly rising. Could this be the predecessor of the human photopic and scotopic response and the log of their ratio correlated to sensation of hue by Homer Tilton (in the middle of the visible spectrum). Merging Tilton, Weber-Fechner, and Judd $Ln(1/Ta)-Ln(1/Tb)=Ln(Tb/Ta)$ The reported red/NIR color ratio in viper vision is also plausible because vegetation emits NIR as a product of the process of photosynthesis. This red/NI color ratio could also compare visible light to 8-12 micron IR region where peak spectral response wavelength=2898 uK/300K=10 u which leads to VT biophysics resonance at 3.5 & 7-11 u by spectral absorption of amino acids.

Producibility of 64×48 mm AM TFT IC Display

But before leaping to 3D and color thermalization for the sightless, one must specify a reasonable spatial resolution and practical dynamic range. Ideally arc-minute resolution defined as 20/20 vision[44] is desirable as well as instantaneous dynamic range of 1000/1 with some adaptive light control over the ambient illumination $10^5$ lux down to $10^5$ lux. Although a single 256 MB RAM IC can store and process as many pixels as the reported 120 million rods and 6 million cones[45] in each retina, which signals from both eyes are compressed to about 1.6 million fibers, the 70 lines per millimeter was the highest resolution found in the human skin. To start 10 lines/mm resolution with VGA 640×480 seemed like a practical compromise to use available display TFT because their heat dissipation has been studied extensively and is compatible with the VT requirements. Amazingly sensibility tests of the human forehead had been made and reported[46] over an area of 37 cm$^2$ consistent with our 6.4×4.8=30.7 and in fact the jndT of 0.001 C-0.002 C was even better than the conservative/safer 0.003 C VT used elsewhere.

[44]Luxemberg, Southall
[45]Lindsay
[46]reference to be supplied

FDA and FCC regulations limit the maximum allowable radiation to one milliwatt per square centimeter and 1 mw/cm$^2$=1 mw/(100 p)$^2$=100 nanowatts/p$^2$ where that pitch p=100 micron=0.1 mm=0.01 centimeter was the target of thermal conductivity research for OPT omnispectramammography photodynamic therapy. 1000 steps would cause an excessive 3 C rise and exceed that limit. However 512 steps of 0.003 C or 1 k×0.0015 C will cause only a 1.5 C rise from nominal skin temperature of 305K to 306.5K and 49 to 50 milliwatts/cm$^2$ according to Stefan-Boltzman power/area=5.67 picowatts/cm$^2$×(T)$^4$. This time rate of heat energy flow by conduction is the power per unit area that is proportional to the temperature gradient dT/dx such that the thermal conductivity×dT/dx=power/area=3.0 mw/cm C×0.33 C/cm=1 mw/cm$^2$. [Note gradient 0.33 C/cm=0.0033 C/p, defines pitch p=0.1 mm for the NET=jndT=0.003 C.]

Promise of 3 Phase Production: a. Gray

Uniform gradations of temperature or steps of 0.003 C degrees are unlikely to match the logarithmic sensory responses known as the Weber-Fechner law of psychophysics. Simply stated if perceived Brightness B=−Log Relative display Luminance, L then dB Ln10=−dL/L>2% visibility. Just noticeable differential brightness jndB=0.02/2.3=0.00868 and let Bmax=512×0.00868 jndB uniform steps=4.447 and Lmin=10$^-$Bmax=35.7 ppm>10 ppm. Accordingly provisions are made in the preliminary design to incorporate a LUT look up table to optimize the gamma or slope in the log vs log transformation and in order to maintain 1000/1 dynamic range with 1.5 C max rise. It is possible that the sensitivity might be twice as good or 0.0015 C as an average of different values reported for pit vipers and humans forehead.

The forehead thermal resistance R in units of (Kelvin) degrees per watt varies the skin temperature slightly from nominal 305K=32 C in response to the nanowatts of power product of TFT drain-source voltage and current, that is modulated by DTV camera video signal, thru match filtering image process with automated quality control feedback, and applied as the TFT gate to source voltage. Furthermore the TFT output structure (voltage source or current drain) lends itself to consideration, in the event thermalization is unsatisfactory, to Maxwell's electromagnetic fields and wave equations[47] as so aptly articulated by Yale Physics Professor Wm Bennett[48].

[47]Elmore, Maxell, Hudson
[48]Bennett

The thermal conductivity K, gradient of temperature $\nabla T$, divergence of temperature gradient $\nabla\nabla T=\nabla^2 T$ ("Laplacian") and diffusivity $D=K/$(specific heat×specific gravity) are more fully described in the Omnispectramammography patent (OPT) and references therein. Suffice it to recall vectors of calculus 101 to exploit $K\nabla T=$power/area, and $D\nabla^2 T=\delta T/\delta\tau$ where $T=f(x,y,z,\tau)$; $\nabla T=\delta T/\delta x+\delta T/\delta y+\delta T/\delta z$ and $\nabla^2 T=\delta^2 T/\delta x^2+\delta^2 T/\delta y^2+\delta^2 T/\delta z^2$. Since there is reported evidence this gradient vector of a scalar function and Laplacian Operation are performed both in the visual cortex and in the tongue signal processing it seems likely to apply somehow to the forehead thermal vision signals. But if not, its easy implementation in image processing tests is well known as a center pixel value minus its nearest neighbors average.

Sparking the VT initial postulate was a remarkable fact that the thermal conductivity of breast cancer almost doubles from typical tissue 3 milliwatts/sqcm/(C/cm) to that of water, 5.56 as if a return to primordial origin. Why not restore primordial thermal vision? But conductivity should have done that long ago, so biophysics resonance better explains the sensible and efficient energy link to brain.

Most remarkably now, relating said conductivity $K\approx 3$ mw/sqcm/(C/cm) at OPT premetastatic 10 pixels/mm resolution revolution of pitch $p=0.1$ mm$=100$ microns, and 10 ppm sensitivity simplifies to 100 nanowatts/p^2/(0.003 C/p) $=K=1/R$ p where thermal Resistance $R=0.003$ C/100 nanowatts. But what watt is the maximum safe irradiation FDA & FCC permit? It is 1 milliwatt/sqcm$=$mw/(10^4 p^2)$=100$ nw/p^2$=(50-49)$mw/sqcm between $[(305K \text{ skin}+0.003\times 512 \text{ jndT})^4-305K^4]\times 5.67$ picowatt/sqcm.♥

♥ Stefan-Boltzman constant 5.67 pw/sqcm and equation.

In brief, the integrated blackbody radiation of the skin at 305 Kelvin is 49 milliwatts per square centimeter (mw/cm².) and this is proportional to the fourth power of Kelvin temperature. Envision a byte of 256 video steps of 0.003 C jndT$=0.768$ C rise. To 49.56 mw/cm². Consider 512 video steps of 0.003 C jndT$=1.536$ C or 1 mw/cm² rise (harmless per FDA) to 50.0 mw/cm². The optimum gamma can readily be determined per Weber-Fechner law of psychophysics and easily implemented with a LUT look up table of video signals to power per pixel.

Viper Vision initial resolution may fall short of 20/20 vision, which by definition resolves one arc minute$=291$ microradians$=2\times 2.5$ micron photodectors/17.18 mm$=0.005$"/17.18" arms reach resolution of 200 dots/inch. The fovea part of the retina has the highest resolution but only over an angle of 5×5 degrees$=5\times 60=300$ arc minutes or 300× 300 pixels. Fast fixation is very similar to the snap action focusing of pit vipers. To overcome macular degeneration, recent "retina implants" of a silicon chip converting photons to electrons has been reported.

The remaining 0.003 C jndT just noticeable differential Temperature is consistent with the "micro-reciprocal degree" sensitivity $[=10^{\wedge}6(1/T_1-1/T_2)]$ in the locus of blackbody radiation color temperatures in color space. Hence field sequential color for the blind could be practical reversal again of Onmispectravision if human factors experiments indicate merit and utility of true color transformations to IR. Monochrome VT alone would be milestone achievement and depth perception would be next important achievement. If dogs can be trained to guide the blind why not restore or retrain the pit viper vision innate in humans except as fever indicator.

To produce 3D stereoscopic vision[49] for those blind people accustomed to distance monitoring with a cane, it is further postulated that a lateral image shift could replicate the triangulation and half arc minute disparity that spans the nominal 65 mm interpupilary[50] distance, comparable to a bandaid width above and compatible with desirable 100 micron resolution and ubiquitous VGA 640×480 pixels. Alternative to stereoscopic camera for ranging replacement of blind persons stick, a near-IR illuminator (LED) could "range gate" slices of the forward volume.

[49]NAS National Academy of Sciences
[50]Southall Physiological Optics

Beyond IR Color Temperatures for Sightless:

Inexpensive video cameras with resolution of VGA PC 640×480 on 64 mm×48 mm is practical good start but 10 pixels/mm$=100$ micron pitch (p) might need optimization or camera zoom subject to human (viper vision) factors to be evaluated. If so this quasi-retina would allow redundancy and fault tolerance or novel color scheme. Some Projection TV and virtual image eye-glass displays employ TFT with this 640 dots/inch or better whereas direct view TFT are limited presently to about 200 dots/inch.

Promise of 3 Phase Production: b. Color

The Color of Nature Teaches the Nature of Color©.[51]. Color vision for the sightless should not be false color or gilding the lily but "flypaper" to catch sponsors such as TV advertisers offering new access to some 10-37 million visually impaired customers. Color VT would also be convincing color closure and concrete evidence of the math and morphology of extra-spectral magenta Stapleton set out to find though blind to its beneficial impact for the blind until asked 4 times to provide vision for the sightless. To convey the concept of color to those blind since birth is different than to those who became sightless to various degrees after learning colors. The compensation by other senses, as developed and described by Helen Keller, suggests they could be correlated with the color of nature so as to teach the nature of color using vision thermalization.

© Copyright title of a book by J. J. Stapleton, Pte. et al, a work in progress (Vantage Press NY)
[51]The Color of Nature Teaches the Nature of Color© Copyright title of a book by J. J. Stapleton, Pte. et al, a work in progress (Vantage Press NY)

If the common names of colors of fruits and vegetables can be associated with the sensations of their touch, taste and/or odor and correlated with the skin temperatures generated in vision thermalization from camera video signals of said foods, then the visualization of the world of color by the sightless would be enhanced more than color TV enhanced mono-chrome black & white TV 50 years ago. Newton's rainbow out of the prism ROYGBIV might become Red apples and tomatoes, oranges, yellow bananas, green beans and peas, blueberries, and violet eggplant.

Thus the siren of a fire truck correlated to the color temperature of red apples would evoke the mental image of a red fire truck. Newton also postulated visual vibrations saying color is to light as pitch is to sound but video to audio converters have not prospered for some reason, perhaps due to ten octaves of sound but less than one of visible light. However this VT process should not be the reverse of pseudocolors assigned arbitrarily to temperatures or arbitrary gray levels but more like the reverse of omnispectravision conversion of 3 IR bands to RGB. At a minimum, the locus of color temperatures, in the CIE x,y chart from red hot to white hot to blue would differ radically from custom of blue representing ice cold. As a matter of fact recent review of the discrepancies between the sensitivities expressed in just noticeable microreciprocal degrees $(10^{\wedge}6)(1/T_1-1/T_2)$ and jndT 0.003 C finally related these disparate measures of light and heat, as DB Judd probably realized 70 years ago.(JOSA) Instead of sensing temperature T or difference dT, Judd implies humans sense the difference in reciprocal temperature ($\perp$ or $1/T$) which is equivalent to the Weber-Fecher Log response of the senses since $\mathrm{Ln}(T) = \int_1^T (1/x)dx$ Not to seem pedantic, but to be more articulate for many disparate sciences in conversion of color vision for the sightless, one can apply college calculus 101 If $y=x^N$ then the derivative readers recall $dy/dx = N\, x^{(N-1)}$. Thus for heat signal flow calculations in the brain as in math below it is helpful to realize: derivative of sphere volume $4\pi r^3/3$, $dV/dr = 4\pi r^2$ = surface area and derivative of circle area $\pi r^2$, $dA/dr = 2\pi r$ = circumference (edge) and derivative of circumference $2\pi r$, $dC/dr = 2\pi$ (radian), dot or pixel.

Accordingly, let vertical axis y be W watts of power/area under Planck's blackbody curves, s stefan boltzman constant (usually sigma=5.67 picowatts per sq cm) and let x horizontal axis be absolute, Kelvin Temperature T=Celsius+273.16 C Stefan Boltzman formula for integrated power of black body over the entire spectrum of wavelengths per unit area $$W = s\, T^4.$$

taking the derivative with respect to Kelvin temperature, T, $$dW/dT = 4\, s\, T^3$$

rearrange then divide both sides by W:

$$dW = 4\, s\, T^3\, dT$$

$$dW/W = 4\, s\, T^3\, dT/(s\, T^4) = 4\, dT/T$$

$$(300.003/300)^4 = 1.00004 = 4 \text{ times } dT/T \text{ of } 1.00001$$

But then the heat sensitivity would be 4 times worse than dT indicates or 40 parts/million whereas several reports of dT is 0.001 C or 0.002 C vs VT conservative 0.003 C from ScAm 1980.

$$\text{Wien law: Wpeak} = 1.29\, T^5 \text{ femtowatts/cm}^2/\text{micron}$$

again take derivative $$dW_{peak}/dT = 1.29 * 5\, T^4$$

$$dW_{peak} = 1.29 * 5\, T^4\, dT$$

$$dW_{peak}/W_{peak} = 1.29 * 5\, T^4\, dT/(1.29\, T^5) = 5\, dT/T$$

Hence instead of sensing the heat or integrated area beneath the Planck black body curves per stefan boltzman formula, the viper vision must sense selective spectral radiances (color beyond rainbow) that is the curve of the W per unit wavelength which is very low but rises very very fast in the visible and near infrared. Most IR engineers concentrate on the flat region of each spectrum about Wpeak at "wavetemp"=wavelength$\lambda \times T$ Temperature=2898 micron K. Color ratios of the IR spectra account for the fantastic sensitivity, much better than monochrome contrast ratio or area under Planck curve.

Plancks' Blackbody Radiation Re-Formulation for IR Color (Spectral) Vision:

$$W = c_1/\{\lambda^{-5}[\exp(hf/kT)-1]\};\ c_1 = 8\, \pi h\, c = 4.9925E\text{-}24\, J_m$$

where $kT = 0.026$ ev and for $hf = hc/\lambda > 5\, kT$ the $-1$ can be neglected.

$$W_1 = c_1/\{_1{}^{-5}[\exp(hc/k\lambda_1 T_1)]\} = \{\lambda_2{}^{-5}[\exp(hc/k\lambda_2 T_2)]\}$$

$$W_2 = c_1/\{\lambda_2{}^{-5}[\exp(hc/k\lambda_2 T_2)]\}\ \{\lambda_1{}^{-5}[\exp(hc/k\lambda_1 T_1)]\}$$

$$\mathrm{Ln}(W_1/W_2) = 5\, \mathrm{Ln}(\lambda_2/\lambda_1) + (hc/k)[1/\lambda_2 T_2 - 1/\lambda_1 T_1]$$

for one $\lambda = \lambda_1 = \lambda_2$ $$\mathrm{Ln}(W_1/W_2) = (hc/\lambda k)[1/T_2 - 1/T_1]$$

let $[1/T_2 - 1/T_1] = 10^{-6} = \mu\text{-reciprocal degree}$ $hc/k = 0.014395$ let $\lambda = 1$ micron $= 10^{-6}$ $$\mathrm{Ln}(W_1/W_2) = (hc/\lambda k) 10^{-6} = 0.014395/\lambda \text{ microns}$$

$W_1/W_2 = \exp(0.014395) = 1.0145$ i.e 1.45% for 1μ-reciprocal degree

For the max allowable 1.5K rise note $1/305 - 1/306.5 = 6.44$ μrd then $W_1/W_2 = \exp(0.014395 * 6.44) = 1.10$ or 10% variation Quantizing to 10 bits, $10\%/1000 = 0.000010 = 10$ parts/million jndT:QED!

Also choose $\lambda_2 T_2 = \lambda_1 T_1$ so $\lambda_2 = \lambda_1 T_1/T_2 = 305.003/305.000$ $$\mathrm{Ln}(W_1/W_2) = 5\, \mathrm{Ln}(\lambda_2/\lambda_1) + (hc/k)[1/\lambda_2 T_2 - 1/\lambda_1 T_1]$$

simplifies to $\mathrm{Ln}(W_1/W_2) = 5\, \mathrm{Ln}(\lambda_2/\lambda_1) = \mathrm{Ln}(\lambda_2/\lambda_1)^5$ thus $W_1/W_2 = (\lambda_2/\lambda_1)^5 = 1.00005 = 50$ppm power for jndT 10 ppm $\lambda_2 = \lambda_1 T_1/T_2 = \lambda_1 306.5/305.000 = 1.005\, \lambda_1$ for max 500 jndT=1.5K $W_1/W_2 = (\lambda_2/\lambda_1)^5 = (T_1/T_2)^5 = 1.005^5 = 1.025$ or $2.5\% = 500$ jndT for example $1\, u \times 306.5 = 1.005\, u \times 305$ and $2\, u \times 306.5 = 2.010\, u \times 305$ It is best to avoid absorption bands of water, oxygen, carbon dioxide so the preferred wavelengths for peak transmissions from the VT TFT to the skin would be 0.85, 1.0, 1.6, 2.2, and especially 3.5-4.0 and 8.5-12.5 microns for amino acids resonance.

In other words, the above interdependence of light and heat, power, wavelength and temperature comes clearer the eye-brain biophysics resonance that finally brings color closure over entire spectrum and extraspectral magentas—such that the Land 2 color theory and vipers 2 color vision gives clue of hue and hint of tint in the vision for the sightless. Re-presenting true color fidelity via VT to the sightless also requires much better comprehension and transformation of complementary colors over the entire spectrum so that their compensatory neutral sum is conveyed to the blind. Accordingly the midspectrum greens need a definitive conversion. In CIE color space the straight line joining UV to IR is the extraspectral magenta region represented by x,y color coordinates such that $$y = 0.48x - 0.08.$$

FIG. 7d illustrates how each point along the magenta line the slope (m) of another straight line thru equi-energy white 1/3, 1/3 pivot point can be computed and used to determine the y-intercept (b)—except for the one point of magenta $y=0.48/3-0.08=0.08$ directly below 555 nm at 1/3, 2/3 where the slope is infinite. The lines are truncated along the horseshoe or tongue shape locus of wavelengths which point defines the complementary color (green) of the magenta starting point of each line.

Figure 3C:
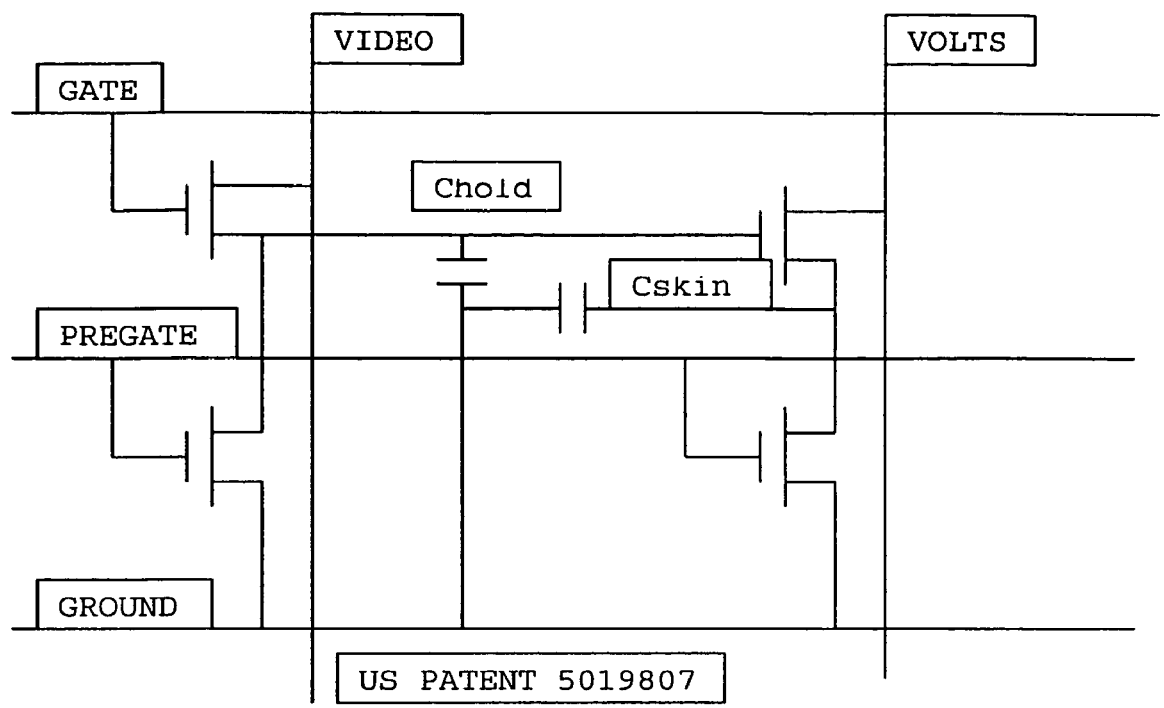
FIG. 3a is a detailed analytical diagram of the VT voxel, i.e. 3D pixel volume, (0.1 mm)^3 derived from prior art formulas therein and practical compromises.
FIG. 3b shows slow rise or fall times in simplified TFT sharpened in FIG. 3c circuit schematic of totempole pair of TFT for higher frame rates with minor adaptation from J&B Stapleton flexible display screen U.S. Pat. No. 5,019,807.
Figure 4A:
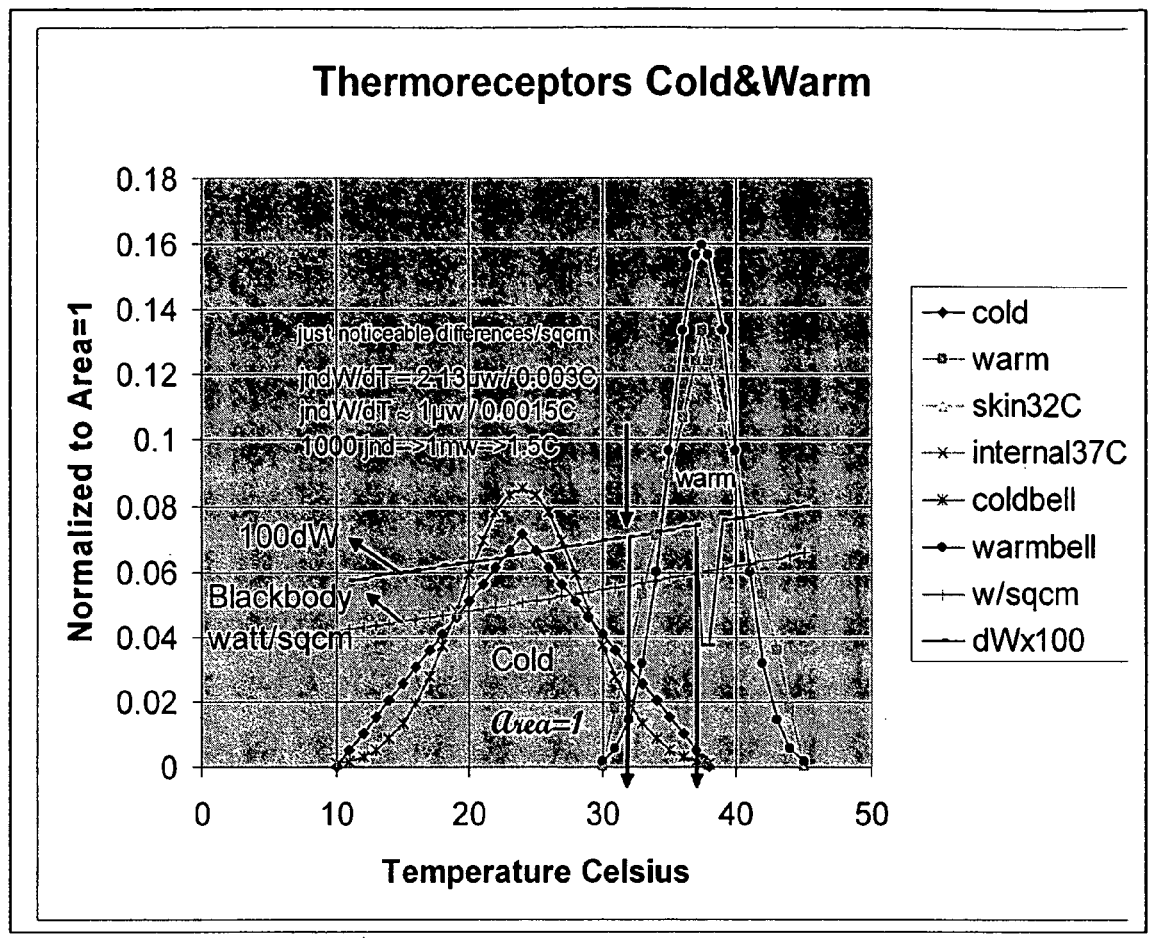
FIGS. 4a & 4b are graphic representations derived from reported cold/warm receptors temperature spread and distribution data[19]. Because several recent textbooks in physiology, anatomy[20], biophysics, nervous system, and numerous internet documents indicate that very little is known about the two types of thermoreceptors beyond the cold receptors sensing between 10-38 C and the warm receptors sensing between 30-45 C,[21] FIGS. 4a & 4b graphical deductions particularly in their overlap region around the typical skin temperature of 32 C provides some novel insight and fair analogy to the eyes Photopic and Scotopic visual responses.
Figure 4B:
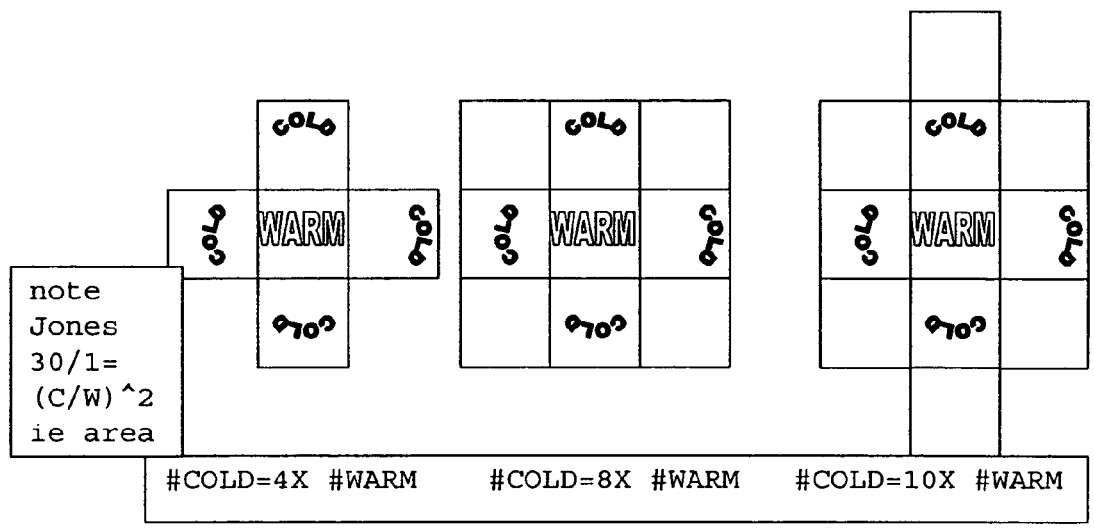

VT 3-color IR for the blind, once proven meaningful, would not be much more expensive than monochrome due to economies of scale of RGB over B/W. Chrominance is defined within triangle of RGB phosphor or LCD filter color coordinates (x,y,z) where z is implicit because x+y+z=1. Similar to our 3 color IR Omnispectravision, 3 bands $\partial\lambda_3 > \partial\lambda_2 > \partial\lambda_1$ preferentially absorbed by amino acids at $eV_3 < eV_2 < eV_1 = 1.24$ μm/$\lambda_1$ all of which will be optimally mapped as color ratios for the Blackbody irradiances $H_j = H(\lambda_j)/\Sigma\ H(\lambda_j)$ for j=1,2,3. FIG. 3a and FIG. 6 illustrate the electromagnetic[52] and blackbody radiation[53], conduction and diffusion of the heat flow from the TFT signals generated in the LUT look up table as a function of the video camera luminance and chrominance signals to the skin.

[52]Maxwell, Bennett
[53]MIL-IR, Hudson

Note: due to multidisciplines use of same symbols for different terms need to be understood in context and/or with following notations. Let capital C°=Celsius degrees, C'=specific heat calorie/gm/C° and C=Capacitance=∈A/d charging to "action potentials">26 mv thermal noise kT where k=1.38×10$^{-23}$ joules/Kelvin (unit of entropy). Unfortunately confusion arises because Thermodynamics[54] is a misnomer since historically it deals with the static, steady state equilibrium and not the transient thermal analysis of heat flow used in VT. Accordingly modern scientists call it thermostatics and speak of the dynamic heat flow in terms of radiation, conduction, convection etc. Likewise in electrostatics, so called electromotive force is not a force. How each picture element of temperature "moves beyond itself"[55] [7 p^2 per second] is precisely the counter-intuitive crux of VT challenge to show the proof of principle and feasibility of this approach in Vision Thermalization. The diffusion equation definitely overcomes the reported spatial limitations of the thermoreceptors because they typically used the static, steady state "two needle" or "two probe" test to resolve the separation (say dx) between two points at given temperature (T).

[54]Abbott, Alberty, Hill, Reiss
[55]what diffusion means to Pop Physics STEP student in Bronx N.Y.

Amount of power flowing (heat energy per unit area and unit time) from TFT coupled by blackbody radiation and conduction thru the left face of cube FIG. 3a is $$-K\ d[T - \partial x\ dT/dx]/dx = -K\ dT/dx - \partial x\ K\ d^2T/dx^2$$

where the 2$^{nd}$ term—$\partial x\ K\ d^2T/dx^2$ is the amount of heat per second added to the cube. With specific heat C', the thermal capacity of unit volume V is C'(1×$\partial x$) and the rate of temperature rise per unit area is C'$\partial x$ dT/dt. Thus we (Schaum's) will prove below Fourier-Fick formula:

$$C'\partial x\ dT/dt = \partial x\ K\ d^2T/dx^2\ \text{and}\ dT/dt = \text{Diffusivity}\ D\ d^2T/dx^2$$

where Diffusivity D=Conductivity K/(Sp.Heat C'Sp.Gravity)

Expanding to 3 dimensions dT/dx becomes gradient $\nabla T$

Power/Area $A = K\nabla T$ and Watts=$AK\nabla T$ joules/sec $D\nabla^2 T = \nabla \cdot (K\nabla T)/(\text{Sp.Heat C'} \times \text{Sp.Gravity}) = \delta T/\delta t$.

For FDA, max mw/cm$^2$=100 nw/p$^2$; where OPT pitch p=0.1 mm=100μ,

Conductivity K=0.003 w/cm$^2$/C°/cm=100 nw/p$^2$/0.003 C°/p

Thermal Resistance R=1/Kp=0.003 C°/100 nw=3×10$^4$ C°/watt vs 10$^7$ Ω.

$K\nabla T$=Power/Area $A = W_{sb} = \sigma T^4 = \Pi = E$ v/m×$H$ a/m $KA\nabla T$=Watts=dQ/dt=mass C' dT/dt=density×volume×C' dT/dt dQ(heat energy)=mass C'(sp.heat)dT=T dS(entropy)=

=(10^$-2$ cm)^3×gm/cc×0.003 C°×cal/gm/C°×4.2 j/cal=12.6 nj 12.6 nj=12.6 nwatt sec=126 nw (0.1 sec)=90 nw (0.14 sec)=

=378 nw(1/30)sec assuming initially TV 30 frames per second.

Diffusivity D=Conductivity K/(density×Sp.Heat C')=

=3 mw/cmC°/(gm/cc×cal/gm/C°×4.2 j/cal)=7 p^2/s $D\nabla^2 T = (p^2/0.14\ \text{sec})\nabla^2 T = \delta T/\delta t = KA\nabla T/(C'\ V\ \text{density})$:

NOTE 1$^{ST}$ time derivative, not 2$^{nd}$ as with the IR electromagnetic fields[56];

[56]EMF Bennett, Masxwell, Jordan $c^2 \nabla^2 E = \delta^2 E/\delta t^2$ and $c^2 \nabla^2 H = \delta^2 H/\delta t^2$ where E=∇Voltage $c^2 = (\lambda f)^2 = 1/\mu \in = 1/(\text{permeability} \times \text{permittivity}) = \text{Energy/mass} = hf/m = hc/(\lambda m)$ and $E/H = \sqrt{(\mu/\in)} = $Impedance Z Resistivity ρ=1/conductivity σ and Resistivity× Permittivity=ρ∈=∈/σ=Resistance× Capacitance=Time Constant τ=1/ω=30 usec; C/A=1 ufd/cm^2=100 pf/p^2; (W F Bennett) Current density J=σ E=I/A and $J/C/A = (I/A)/(C/A) = I/C = $dv/dt$\approx$10 na/100 pf=10 mv/100 μs=kT/260 μs The noise equivalent thermoelectric energy in capacitance C is CV$^2$/2=100 pf(26 mv)$^2$/2=33.8 fj<<12.6 nj necessary to heat one forehead voxel p$^3$ up 0.003 C.°=jndT as explained above and recapitulated below because traditional Thermodynamics only treats the simpler, static, steady state where dT/dt=0 and the Poisson equation reduces to the Laplacian equation $\nabla^2 T$=0. The purpose of this transient thermal analysis is definitely not to befuddle with bs or baffle anyone with brilliance or pedantic pretense, but rather to definitively address and emphasize the fact that everyone would be sightless in the static "steady state" without the eyes saccadic sampling by herky-jerky movements (as more fully explained and exploited in our Sparkle VVTD patents.)

Defining at any time t the temperature T=T(x,y,z,t) at any point (x,y,z) within a forehead volume v (approximately 64×48×3 mm) having a surface area s, and given constant density=mass/volume=m/v, specific heat C' calorie/gram/C°, thermal conductivity K, and Diffusivity D=K/(C' m/v), the gradient of scalar temperature $\nabla T$ (read del T) is a vector in direction of maximum rate of temperature change in space, $\nabla T = \delta T/\delta x + \delta T/\delta y + \delta T/\delta$ and divergence of temperature gradient vector, $\nabla \nabla T = \nabla^2 T = \delta^2 T/\delta x^2 + \delta^2 T/\delta y^2 + \delta^2 T/\delta z^2$ where $\nabla^2$ read "Laplacian" or del squared) is the scalar net outward flux or flow such that $K\nabla T$=power/area, and $D\nabla^2 T=\delta T/\delta t$ The skin's ganglion cells, as well as the retina and visual cortex, and digital image processor routinely do this edge enhancing, "del squared" Laplacian operator simply within each 3×3 array # by subtracting from the center pixel value the 8 nearest neighbors average. The center maybe an excitor or inhibitor and the neighbors are the opposite. With several standard methods of solving such differential equations, it can not be over emphasized that initial conditions are absolutely essential and all the formulas are useless, ambiguous, or "chaotic"[57] without them. Hence the VT R&D search for initial conditions of vision. Whereas the solution to the heat wave equation is said to be parabolic, the solution to electromagnetic differential wave equations is elliptic. Suffice it to say here that the notion of EM and heat waves or vibrations is treated with complex exponentials (such as $e^{(x+jy)}$ or equivalent Fourier Series of real number×cosine($\omega t+\theta$) and imaginary number×sine($\omega t+\theta$) and preferably by discrete, finite mathematics in computer.

[57] Mullin, Gleick

The integral form shed s more light on heat transfer[58] and transformation.

[58] Holman, J P, Heat Transfer McGraw Hill 1986; &Thermodynamics texts

1. Power Out (watts)=$\iint(-K\nabla T)\cdot n\ ds$, where n is normal (perpendicular)
2. Power In (watts)=$\iint(K\nabla T)\cdot n\ ds=\iiint[\nabla\cdot(K\nabla T)]dv$
3. Heat (energy, joules) within $v=\iiint T\ C'$ m/v]dv therefore
4. Power, that is, time rate of increase of heat=$d/dt[\iiint T\ C'$ m/v]dv=$\iiint[(dT/dt)C'$ m/v]dv
5. Equating right parts of 2 and 4 above $\iiint[\nabla\cdot(K\nabla T)]dv=\iiint[(dT/dt)C'$ m/v]dv and rearranging $\iiint[(dT/dt)C'$ m/v$-\nabla\cdot(K\nabla T)]dv=0$ 6. But because volume v is arbitrary the last integrand within brackets must be identically zero so that $(dT/dt)C'$ m/v=$\nabla\cdot(K\nabla T)$ and 7. $dT/dt=(K/C'\ m/v)\nabla\cdot(\nabla T)=D\nabla^2 T$ Q.E.D.

They are more fully described in the Omnispectramammography patent and references therein. Most remarkably now, relating said conductivity $K\approx 3$ mw/sqcm/(C/cm) at OPT premetastatic 10 pixels/mm resolution revolution of pitch p=0.1 mm=100 microns, and 10 ppm sensitivity simplifies to 100 nanowatts/p^2/(0.003 C/p)=$K=1/R\ p$ 1 milliwatt/sqcm=mw/(10^4 p^2)=100 nw/p^2=(50-49)mw/sqcm between [(305K skin+0.003×512 jndT)^4-305K^4]×5.67 picowatt/sqcm. ♥

♥ Stefan-Boltzman constant and equation.

Due to the fact vision is in the mind and the complex signal processing boundaries within the eye-brain are not so clearly delineated, some maybe blind due to the mind, rather than eye disorders ands thus may not be aided by VT.

Sense of sight is in the eye, which is easily mimicked by a TV camera whose signals had been transformed to various alternative means of stimulation for crude sight using Hughes scan converters (Huelsman, Stapleton 1972).

For the same exposure (=energy/area) the IR heat wavelength of 10 microns has 20 times the number of green photons near 0.5 microns and thus the IR signal to noise ratio is $\sqrt{20}=4.5$ times greater than green.

Because all human sensory signals are co-located, combined, compared, contrasted, correlated and colored in one part of the brain called the superior colliculus, it should likewise process the VT signals that the nervous system conveys from the forehead. Electric properties, i.e. proportionality constants are not constant in the body. Biologic tissue contains free charge carriers and bound charges leading to both electrical conduction and dielectric effects respectively when a potential gradient is applied. Heating appears to be the dominant biologic mechanism in frequency range of 10^4-10^5 Hz. From 10^3-19^5 displacement current is substantially less (40-70 db) than conduction current and often neglected. Around the 50 Hz peak sensitivity electrolysis predominates and in between the high and low frequencies the neural stimulation dominates.[59]

[59] heating frequencies

To most engineers heat is wasted energy. TFT seemed natural because their heat dissipation has been studied extensively and is comparable to the VT requirements. The invisible but "observable" product of TFT current and voltage across the drain and source ($V_{ds}$) is the unusable power normally wasted in excitation of the LCD or OLED, which display media are omitted in the VT. The TFT power dissipation was the major problem of the past; here it is a probable solution for sight, more accurately for thermal vision restoration, reverse evolution to root vision, or reverse engineering of natural history.

Indeed there are rod-shaped and cone-shaped receptors in the skin and more remarkably ganglion cells which not only combine and compress the signals as in the retina but actually effect the Laplacian operator in that an exciter cell is surrounded by inhibitor cells as nearest neighbors and inhibitor cells are surrounded by exciter cells. The same 3×3 # operator was exploited to enable HDTV to Sparkle with all 2 million dots on old analog TV sets and this might triple our initial 10/mm. But if the highest 70/mm tactile resolution reported or better proves useful then our proposed Intelepresence UHD ultra high definition 16,000×9,000 can match the eyes capacity and Intel challenge. The forehead thermal resistance R in units of (Kelvin) degrees per watt varies the skin temperature slightly from nominal 305K=32 C in response to the nanowatts of power product of TFT drain-source voltage and current, that is modulated by camera video signal, thru match filtering image process with automated quality control feedback, and applied as the TFT gate to source voltage, Visualization of the world of color by the sightless would be enhanced more than color TV enhanced mono-chrome black & white TV 50 years ago. Plancks' blackbody radiation[60] formula:

[60] Planck in Shamos $W=c_1/\{\lambda^{-5}[\exp(hf/kT)-1]\};$ where kT=0.026 ev and for hf=hc/$\lambda$>5 kT the −1 can be neglected.

Hence instead of sensing the heat or integrated area beneath the Planck black body curves per stefan boltzman formula, (5.67 pw/cm²T⁴) the viper-like-vision VT will create the sensation of selective spectral radiances (color beyond rainbow), that is the curve of the W per unit wavelength which is very low but rises very fast in the visible and near infrared.

Recall color ratio $W_1/W_2=c_1/\{\lambda_1^{-5}[\exp(hc/k\lambda_1 T_1)]\}/c_1/\{\lambda_2^{-5}[\exp(hc/k\lambda_2 T_2)]\}=\{\lambda_2^{-5}[\exp(hc/k\lambda_2 T_2)]\}/\{\lambda_1^{-5}[\exp(hc/k\lambda_1 T_1)]\}$; let $\lambda=\lambda_1=\lambda_2$ or $\lambda_1 T_1=\lambda_2 T_2$ Promise of 3 PhaseProduction: c. 3D Alternative Cane after 3D Braille Although 3D depth perception is not needed for vision thermalization (VT) for the sightless to "see" TV ads, it is essential for them to walk without the white cane, to run, ride a bike etc. and to consume many of the products TV advertisers would want to offer some 10-37 million people seriously impaired visually. Color was not essential but previous thermal analysis showed how VT exploits the blackbody formula, the rationale of the micro-reciprocal-degree embedded within Weber-Fechner psychophysics logarithm response[61] of each sense,

[61]FIG. 2d dy/dx of course is very different near x=T=305K $LnT = \int_1^T dx/x$.

Providing the perception of depth for the sightless required a greater depth of understanding human perceptions and especially how a stronger sense compensates a weaker sense as Helen Keller demonstrated and described in her autobiography. At first the thousand to one ratio of video/audio signal bandwidths made suspect the proprietary means and claims of Robert Harris & Associates to re-present TV video scenes by audio descriptors. Braille readers speeds corrected that notion and the audio localization can be clue and cue to direct cameras where to focus.

Further investigation, searching and re-searching revealed the surprising fact that some Braille readers are quicker than the average (sighted) reader (400 vs 350 words/minute). It was no surprise the blind can be bright. It was very encouraging to learn the "hand is quicker than the eye" at least for some Braille readers and magicians. Evidently the 3D display of millimeter (mm) high Braille bumps 2.5 mm apart can be read far faster by the fingers tactual or tactile sense than the published spatial and temporal frequency limitations. This bodes well for vision thermalization especially since Braille signals have been traced thru the visual cortex, which does the Laplacian $D\nabla^2 T = \delta T / \delta \tau$ as the skin does also and the forehead to $dT = <0.003$ C or 10 ppm.

Braille is the Original Dot Com & 3D. Many of the blind are very bright.

Considering the space-time limitations explained before, and the compensatory role of the other senses, such as Helen Keller more aptly described, the remarkable Braille reading rates certainly support the audio descriptors of television that Robert Harris and Lightshare offer. Conversely taste, smell, tactile pressures and temperatures, binaural hearing and other senses altogether probably compensate for dysfunctional sight and achieve, in concert, the usable cognitive capacity.

Based on brief review of Braille performance[62] on average 124 words/minute up to 300 and 400 wpm, our proposed 3D depth perception assumes the sightless can fully exploit the normal cognitive capacity of 50 bits/second described in Silicon Dreams by Bob Lucky. He gives average rates of 360 words per minute (wpm) for reading, 250 listening. 150 for speaking, 60 for typing. Braille reading rates vary widely in many reports but the average of 124 wpm is most often reported and equated by some to 7.5 characters/second. But most characters are defined by the 6 bit code of a so called cell so 6 bits×8 characters per second is very close to the 50 bps norm.

[62]Braille rates

Clearly the reported achievement of 400 words/60 seconds×4 characters/word×6 bits/character=160 bits/second or about 3 times the Lucky's 50 bits/second cognitive capacity. It turned out later others measured as many as 3 fingers are used (by one or sometimes two hands) so that each finger tip has the 50 bits/second cognitive capacity. Note Lucky used 8 bit byte to arrive at 50 bits/second. But before dismissing 50 bps as very low compared to personal computers 10 GHz×32 bits/word, it is good to realize what 50 bps implies. Imagine the 50 stars of the flag being switched between white and blue background. There would be 250 possible patterns per second, but $2^{50} = (2^{10})^5 = (10^3)^5 = 10^{15}$ which means one pattern per femtosecond ($10^{-15}$ second). If an item does not fit the pattern in memory, this misfit per femtosecond ($10^{-15}$ second) is approximately the period for one wavelength of violet light.

Previously Stapleton reported that the difference in photons transit times to the depth of hue that he calculated happen to equal and therefore maybe the formative causation of the periods (250-500 fs) of the quantum visual vibrations of certain amino acids comprising the pigment proteins Dr. J. Nathans measured. More importantly certain enzymes act as catalysts for the photochemistry reactions that is now reported to be $10^{12}$ times faster than rationalized in early days of TV. In other words instead of 300 milliseconds, 300 femtoseconds is more like normal eyes photochemistry processing times, so it is conceivable enzymes in the forehead skin will become quick learners like the Braille fingertips to expedite the vision thermalization signals or be quick to recall and reactivate the pathways of the viper-like-vision from which we humans evolved.

Contrary to questionable 2 point caliper pressure testing of tactile resolution[63] from 48 mm (calf) down to 3 mm (thumb), 2 mm (first finger), with 18 mm on the forehead below the 22 mm median for the sole of the foot, the so called Aβ touch fibers are only 5-12µ and their conduction velocity is 30-70 m/s whereas the "cold" A∂ fibers are finer 2-5µ and the 1.2 ms spike action potential signal travels at 12-30 m/s. The 2 ms spike pulse travels 0.5-2 m/s in the slowest C fibers that are smaller still a 0.4-1.2µ. An initial target of 0.1 mm for VT and previously OPT was based on a nominal cell size of 10µ and 10×10×10=1000 cell cube.

[63]tactile

Thus the extraordinary sense of pressure, as proven with Braille readers, may also convey the vision thermalization signals to the brain, if not the electrical conduction. Further VT hypothesis was that previously calculated diffusivity of 7 $p^2$/second or almost the 8 nearest neighbors, after experiments that showed the exposure threshold drops with the square root of laser pulsewidth due to diffusion equation, is reason to believe thermoreceptors will be responsive to 0.1 mm resolution and stereo disparity accordingly and reason to suspect measurements were made at thermodynamic equilibrium rather than VT transient heat radiation and conduction.

There is information and good reason to believe that Vision Thermalization (VT) can accomplish three dimensional (3D) depth perception for the sightless in several ways well established in prior art for normal vision. Active ranging and passive stereo were researched anew but this time for the sightless. The range-gated NEAR FLIR and pen size stereo CMOS cameras, on sides of eyeglass frames, are two of the preferred means described here that can provide 3D vision of invisible observables. That may seem like an oxymoron except Jonathan Swift defined vision as "the art of seeing the invisible." Observables are defined as indicators of energy in control systems engineering and are not limited to the visible portion of the electromagnetic (EM) spectrum or audible part of the acoustic spectrum, that is light or sound respectively.

Control systems require feedback signals that generate an error signal which is continually or periodically minimized by correcting the feed forward signal such as sonar, ultrasound, radar, or lidar that transmit sound or light, laser etc. and wait for an echo to return. Accordingly both acoustic and EM waves have been used for auto-focusing in cameras and probably have been considered to act as virtual canes for the blind. (Many academic studies are reported on the internet.)

Near FLIR forward looking infrared is such a feedback control system which is near (1-4 meters) in useful "photogated" ranges for the sightless and also near-infrared (NIR) wherein the wavelength λ used is nearest to red EM waves, as opposed to the most common 8-12 micron FLIR. By definition NIR 0.74<λ<2.5μ but the shortest NIR is preferred because of common NIR illuminators and silicon imagers' responsivity to it. VT R&D found the NIR devices for resonance with glucose unique signature in the 2-2.5μ water-window thereby helping diabetics prevent related eye diseases.

Curiously the just noticeable differential angle, jndA of audible angularization is three degrees (3°).[64] This equals the angle subtended by a temporal half minute on a clock, whereas the just noticeable "disparity" in binocular vision (jndV) is a half minute of arc or $1/120^{th}$ of a degree spatial separation of two objects in two retinas from one common fixation point within the central (fovea) vision. This stereopsis provides depth information augmented by other cues such as size comparisons, shadows, occlusion, etc. but not for the sightless. Localization of a source of sound is determined by the difference or delay in duration of travel times to the two ears some 7 inches (=2×radius r) apart thru the head which subtends 3°=52.36 milliradians at a nose-on range R of 3.4 meters, the high point in FIG. 1. It also shows eye and ear temporal and spatial gaps for 3° increments from nose-on. The extra travel length equals r(A+sine A)≈2rA for small angles A in radians=9.3 mm for A=3°=52.36 mr.

[64]audio angle

This difference in travel distance takes 28 microseconds at nominal speed of sound of 331 meters/second[65], which time delay dτ constitutes the temporal resolution and a phase shift dθ where dθ/dt=ω=radian frequency=2πf. This 28 μs is remarkable because f=1/28 μs=35.73 KHz=179% of 20 KHz maximum audible frequency and the wavelength λ=c/f=cτ=9.3 mm is unlikely to bend around the head. Ideally when phase delay is proportional to frequency there is no distortion, which implies a fixed delay thru an electronic amplifier. The classic resolution roll off in the frequency response of the elderly[66], and several of their complaints, had led us to think that adaptive digital delays would be superior to brute force amplification of sound and noise. But that's another topic outside the scope here except prior research offers useful data for 3D VT.

[65]Lindsay uses speed in air, not in head ear to ear
[66]Olson

Sounds directly to the right or left must travel 11 inches=28 cm around the head which takes 844 microseconds. Hence this phase delay limits localization to frequencies below 1/844 μs=1185 Hertz or 1185 vibrations per second and wavelength λ=c/f=331 m/s/1.3 Khz=279 mm that can bend around the head and provide sound shadows. The electronic analog of this audible angle discrimination, which will be employed later, is called a phase-lock-loop (PLL). The Log (df) vs Log (f) is plotted in FIG. 2c for hearing and touch where the tactile frequencies might be Braille or the tap-tap vibrations of the sweeping white cane of the blind. However, the higher frequencies are localized by the differential intensity ($\partial_1 = k_1$) of the sound in accordance with the Weber-Fechner law in psychophysics. This is also the well known Log response of all the senses since the integral, $$\int dT/T = Ln(T) = \int_1^T (1/x) dx.$$

More curiously the audible localization of full surround sound enables the normal viewer to quickly turn the neck and head sideways and thereby see out of the corner of the eye 180° behind with so called peripheral vision. Some say this is not truly vision, but a moving target indicator (MTI) and threat warning system. More significantly, the 3° localization by hearing is comparable to and cue for fixating the full angle 5 degree field of view subtended by the fovea, wherein each of the 400 cone-shaped photodetectors per millimeter (2.5μ) subtend a half arc minute. (Thus 20/20 vision 2 samples/arc minute conforms to sampling theorem)

Two cones (5μ) divided by the nominal focal length (f=17.18 mm) subtend an arc minute=0.291 milliradian (mr) which is defined as 20/20 vision acuity. How many such square pixels $(0.291\ mr)^2$ dissect the forward looking 2π steradian hemisphere? There would be 74.2 million pixels. At 30 frames/second refresh rate, not that VT must refresh like TV, the fundamental video frequency of a picket fence or alternating black and white would be 2.22 GHz/2 which is about 256 times television bandwidth and suggests compression and/or consideration of √256=16 arc minute resolution=4.656 mr=1.86 cm/4 m≈180°/640.

The area of such a hemisphere with radius R of 4 meters is $2\pi R^2 = 100$ square meters so that the maximum allowable irradiance of mw/cm² would imply an unrealistic, battery killer, kilowatt transmitter. What is sensible and practical? Let's temporarily tolerate 1 Kw to compute the design performance parameters which determine the necessary signal/noise ratio and then back track to minimize the transmitter and battery power.

The $(1.86\ cm)^2$ would reflect back towards the Near FLIR sensor 3.46 milliwatts/$2\pi R^2$=34.6 μw/m²=3.46 nanowatts/square centimeter. What would be the sensor aperture or iris diameter, $D_a$ and $F_\# $=focal length f/$D_a$? Assuming diffraction limited spot diameter (Rayleigh criteria) $D_s$=2.44λ $F_\#$ and $D_s/f$=2.44λ/$D_a$=4.656 mr=18.6μ pixel/4 mm focal length=2.44(×1μ wavelength)/0.524 mm aperture and $F_\#$=f/$D_a$≈8. This is comparable to typical eyes 2 mm iris in daylight that opens to about 8 mm in low light. The near FLIR sensor aperture area $\pi(0.0524\ cm)^2/4$ would intercept 7.46 picowatts=7.46 pj/s=38 photons/μs=38 e/μs=6 ac/μs=6 picoampere for 100% quantum efficiency at #ev=1.24/λ=1.24×0.16 aj=0.2 aj=hf as explained by Planck and in prior memos. This 6 pa pixel photocurrent $I_p/C_p$ pixel capacitance about 0.1 picofarad=dv/dt=60 v/s=1 v/(1/60 s) and the energy stored is $C_p V^2/2$=50 femtojoules=7.46 picowatts×6.7 ms of the 16.7 ms TV field time. The roundtrip time to travel 4 m and back is only 26.7 ns, suggesting 37.5 MHz bandwidth for sharp range-gating pulses. Besides the NIR laser illumination acting like an ordinary flash bulb camera, absent light echo returns, the CMOS sensor does not have to look and can discharge the dark current that limits dynamic range until the range gate enables it to integrate the photons from the distance and then "photogate" (dump/transfer) the charge dq=idt=Cdv into memory. The dv is on the order of 1-4 volts per lux second and the quantum efficiency is on the order of 25-90% with fill factors near 50%.

3D Design CONCLUSION

Near FLIR range-gated up to 4 meters can achieve the desired 3D results illuminating $1/8^{th}$ of a watt over the central, fovea vision 640×480 resolution of half-arc-minute as the discrete 2.5μ photodetectors in retina. Halving the range to 2 meters reduces the power 16-fold to 8 milliwatts due to $1/R^4$ law. In addition to the binocular (5.3×4 degrees) pencil size TV cameras along the sides of eyeglass frames, the laser diode, APD avalanche photo diode, and wide angle camera is practical and affordable with low cost, low power, light weight, high performance of new CMOS imagers. Several reputable companies have indicated an interest and that they are ready, willing and able to supply us CMOS VGA sensors and VT.

The VT IC itself, namely the active matrix TFT thin film transistors, is a proven product over 30 years since Dr. T. Peter Brody[67] invented them to address electroluminescent displays and then LCD, which VT will use without the liquid crystal. Collaborator "Doc Brody" also contributed to StapleVision's patented fault-tolerant TFT for large screen displays. VT is another helpful product of The Total Image Process© far beyond original academic quest for color closure. It was first successful with Omnispectravision by analogy between infrared imaging thermal vision devices and pit viper vision, tho' at the time in early 1980's both were considered to be nonimaging systems.

[67]Coutts, also Brody & Luo in SID Publications & Patents
© The Total Image Process is copyright and service mark of John J. Stapleton, Pte. and title of PhD R&D.

VT R&D has yet to identify the specific thermo regulating proteins combination of amino acids but there is a valid and useful analogy to those in the retina so as to efficiently couple via biophysics resonance the IR (heat) instead of light. The transmission curves in IR for most of the amino acids (comprising proteins that regulate body temperature) are quite similar in the regions noted in last report, so the one for proline was transformed to absorbance (=density=Log(transmission)) where the peaks suggest significant energy-efficient coupling by biophysics resonance to the black body radiation—analogous to amino acids visual vibrations Dr. Nathans measured at JHU.

One might have already noted, typical use of parameters for water instead of body data when not readily available. Well there's only a 4% error in prior computations of diffusivity=conductivity/(specific heat×specific gravity) i.e. water 4.18×1 vs body 3.49×1.25.

Although no second source was found for the reportedly poor spatial resolution of thermoreceptors[68] that was mentioned above, the fact that L. Jones at MIT Dept Mechanical Engineering also refers to the Kenshalo[69] data others use with sqcm or sqmm, and speaks of the "area summation" as constant product of area and temperature rise definitely implies static thermal equilibrium that needs more consideration in terms of the diffusion rationale offered by VT R&D but can not corroborate yet in literature searches. [Said consideration is graphically shown as Regulation at Constant Power (=Power/Area×Area Resolution). Although radiated power/area (emittance) rises with $4^{th}$ power of Kelvin Temperature, its linear rise above 32 C=305.16 Kelvin times the resolvable area inverse relation equals a constant product of power shown as ten times the milliwatts for scale purpose. In order to combine several plots the X axis is changed to deg C and the prior art X values are plotted as dependent Y axis. To fit better the degC/sec was multiplied by 60 to read degC/minute, which hyperbolic rise with small delta-T is major concern.

[68]thermoreceptors/mm University of Bristol Author: Department of Anatomy Malngret F, Lauritzen I, Patel A J, Heurteaux C, Reyes R, Lesage F, Lazdunski M, Honore E. Institut de Pharmacotogie Moleculaire et Cellulaire, CNRS UPR 411, 660 route des Ludoles, Sophia Antipolis, 06560 Valbonne, France.ipmc@ipmc.cnrs.fr Peripheral and central thermoreceptors are involved in sensing ambient and body temperature, respectively. Specialized cold and warm receptors are present in dorsal root ganglion sensory fibres as well as in the anterior/preoptic hypothalamus
[69]Kenshalo Since a million axons are reported for the skin as well as the retina, instead of 400 cones/mm=2.5 micron photodetectors, there is reason to believe 10/mm thermal resolution was fair estimate to start, given tactile 70/mm especially because of the spatial interpolation and differentiation by the ganglion cells in skin (as in retina) that is typically depicted like overlapping Venn (set) diagrams. Thus if the million axons were uniformly distributed (we know they are not)

$10^6/1.8$ sq meter=1/1.8 sq millimeter=0.555/sq mm= $(0.75/mm)^2$

And if there are 30 times more "cold" receptors, vs 4-10 times reported elsewhere, than "warm" then $16.65/sqmm=(4/mm)^2$ and probably >10/mm on forehead. To be demonstrated asap to optimize maximum useful resolution. Accordingly, one might wonder whether negative or positive video is better, which is trivial in the LUT look up table, but critical in the TFT use as source follower or common source with 1 megohm (MΩ) between source and ground or between Vdd and drain. As with most human factors experiments and ergonomic analysis, the instrumentation and measurement methods are too often omitted so the data may be misunderstood or misconstrued.

The best validation and verification to date comes from the realization that the FCC and FDA limit of 1 milliwatt per square centimeter is entirely consistent with the thermal conductivity and reported 0.003 C jndT just noticeable differential temperature (50% feel and 50% do not feel) and our (0.1 mm)^3 voxel. But how then can the maximum allowed power/area be the minimum detectable signal? Duty cycle is key in VT as in film exposure, flicker-free TV, radar, sonar, ultrasound etc etc. For the same exposure, Peak power can be 1000 times higher for $1/1000^{th}$ duration, or more exactly with ten bits of IR video, 1024 times higher for $1/1024^{th}$ of the duration, such that static, equilibrium threshold levels drop to $1/32^{nd}$ due to diffusion.

For any square centimeter: milliwatt× second=millijoule=watt×millisecond

For any (0.01 cm)^2 pixel:100 nanowatt×sec=100 nanojoule=100 µwatt×millisec.

The 1000 jndT/2=1.5 C max was chosen because of concern for 3 C rise to 35 C=95.6 F skin temperature, which would still be 3 F below normal internal 98.6 F=37 C. For mw/cm^2=100 nw/p^2 for p=0.1 mm let 100 nw=10 na×10 v and for 100 µwatt=10 µamp×10 volt=(10 volt)^2/1 MΩ Recall I/C=dv/dt=10 µamp/100 picofarad=10 volts/100 µsec and the time constant RC=MΩ×100 pf=100 µsec and 10-90% risetime=220 µsec<<millisec.

.KVT=3 mw/cmC*0.003 C/0.1 mm=power/ area=σT^4=E (v/m)×H (a/m)

E=<10 v/0.1 mm=100 kilovolt/meter->1 mv/m @60 Hz (W Bennett)

->10 mv/m=1 µv/0.1 mm @600 Hz

Basically VT must enable measurements of the forehead thermal MTF modulation transfer function, that is to say the induced sinewave delta temperature profile vs spatial & temporal frequency or find it in more exhaustive literature searches. Thus to measure performance and production reliability VT, as shown in FIG. 9, also incorporates offline and realtime feedback command and control for Laboratory and factory testing such that a SuperVisor also sees comparable to VT perceptions of user, color TV in LCD A=B, i.e. input and output AM-TFT heat via imaging infrared thermal vision IIRTV thru image memory processor IMP feedback control & calibration of #FPS frames per second, FSC field sequential color and AQA automated quality assurance adapting gamma LUT look of table steps of input light to optimum heat levels out.

Thus the present invention realizes the aforenoted objectives, advantages and features, and although the preferred embodiments have been disclosed and described in detail herein, its scope should not be limited thereby but rather its scope should be determined by the appended claims.

Summary Bullets:

A light to heat transducer versatile video transformation system is comprised of active matrix thin film transistors circuitry configured to provide sensible infrared images to produce vision for the sightless and visually impaired with full fidelity, image integrity, color and depth of normal binocular vision within biophysics resonance limits and affordable, cost effective constraints An image processing subsystem provides image quality enhancements eg. adaptive nonlinear grayscale "gamma" correction in look up table LUT thereby optimizing 1024 uniform or nonuniform steps of 0.0015 C within maximum temperature rise of 1.5 C and. 1 mw/cm^2 difference such as between 306.5 and 305 C nominal skin temperature The IMP image memory processor also provides buffer storage for variable refreshing rates of images to exploit diffusivity and optimize the peak and average power dissipation within the 1 milliwatt per square centimeter maximum allowable radiation (FCC/FDA)

The processor is further designed to provide without objectionable aliasing or flicker remarkably higher resolution than is ordinarily expected by thermoreceptor cells in thermal equilibrium and by Nyquist sampling theorem and averaging circuits thereby exploiting thermal diffusion, and the edge-enhancer Laplacian operator mechanized as the difference of a pixel value and its nearest neighbors average in the image process electronics as well as in the ganglion cells and amino acid inhibitors and excitors in biophysics resonance with the infrared images transformed from light waves or conventional video signals.

VT offers huge new commercial markets by enabling technology for the sightless to "see" PC displays, internet, palm pilots etc. thereby vastly expanding the benefits of the American Disability Act (ADA)

Initial VT AM-TFT is modest, 640×480 VGA resolution in picture of heat photons transformed from light photons allowing further versatility in expandability up to the fullest possible sensation of realism such as 65K×65K pixels of MPEG or UHD ultra high definition Intelepresence.

VT has timely applications for security and surveillance to empower and optimize the fusion of multispectral sensors for the battlefield visually impaired by natural and enemy obscurants in the "fog of war" including means of extending VT IC IR "display" to in fact monitor the biophysics resonance in near IR with the prefrontal cortex and ultimately remote sense a liar or security threats such as at airports along the lines of mine-reader research at UPENN.

Means to meet commerce desires of VT to empower the sightless to see TV and like video screens or movies so that advertisers will enjoy and support millions of new viewers and completion of the ultimate object of the invention to provide a progressive synergism of the multiple functions of present assistive devices for the sightless and visually impaired.

Last but not least reliability means incorporating feedback command and control for Laboratory and factory testing such that a SuperVisor also sees comparable to VT perceptions of user, color TV in LCD A=B, i.e. input and output AM-TFT heat via imaging infrared thermal vision thru image memory processor feedback control & calibration of frames per second, field sequential color and automated quality assurance adapting gamma look of table steps of input light to optimum heat levels out.

Thus the present invention realizes the aforenoted objectives, advantages and features, and although the preferred embodiments have been disclosed and described in detail herein, its scope should not be limited thereby but rather its scope should be determined by the appended claims.

I claim:

1. A versatile video transducer system providing alternative, supplementary sight to a blind or visually impaired person comprising:
an input receiving a signal corresponding to a video image; and
a matrix receiving said signal from said input, said matrix being formed of a plurality of thin film elements generating an infrared image corresponding to said video image and being constructed and arranged to be placed in contact with a thermal sensitive organ of the blind person so that the blind person perceives said infrared image from said matrix;
wherein said infrared image is generated by said matrix includes wavelengths of approximately 3.5, 7.0 and 11 microns in biophysics resonance with the tuned sensitivities, absorption spectra and the quantum vibrations, rotations and stretching in specific amino acids common to said organ, cortex and retina.

2. The system of claim 1 wherein said video input image is an infrared image.

3. The system of claim 1 wherein said matrix is constructed and driven with voltage and current to generate a infrared image having characteristics that are absorbed by specific elements in the organ, said elements being selected from the group consisting of elements from the skin, elements from the cortex and elements from the retina.

4. The system of claim 1 wherein said matrix is constructed and driven with voltage and current to generate thermal spectral frequencies that include a quantum absorption frequency of a biological element.

5. The system of claim 1 wherein said matrix is constructed and driven with voltage and current to stimulate the resonant frequency of an element of the cortex, skin and retina.

6. The system of claim 1 wherein said matrix is constructed and driven with voltage and current to stimulate the biophysics resonance with the absorption frequencies of a thermally sensitive element of a skin.

7. The system of claim 6 wherein said matrix generates a infrared image at spectral frequencies including biophysics resonance with the absorption frequencies of thermoreceptors, ganglion cells, amino acid inhibitors and excitors within the skin of the blind person analogous to those in retina.

8. The system of claim 1 further comprising mounting means for mounting said matrix on one of the forehead and forearm of the blind person.

9. The system of claim 1 wherein said input receives visible light waves incorporating said image.

10. The system of claim 1 wherein said input receives a microwave, infrared, ultrasound or the like video signal incorporating said image.

11. The system of claim 10, wherein said system converts said light waves and said video signals into infrared images.

12. The system of claim 10, wherein a plurality of transistors receives said infrared images from and further generates said infrared images with specific spectral frequencies.

13. The system of claim 12, wherein said plurality of transistors generates said specific frequency in the range of 3.5 microns to 11 microns.

14. The system of claim 13, wherein said receptor is at least one of thermo-receptors, ganglion cells, amino acid inhibitors, glycine excitors and glutamate excitors.

15. The system of claim 1, wherein said system receives said images in the form of light waves and video signals.

16. The system of claim 1, wherein said means for attaching said matrix to a
thermal sensitive organ of the blind person comprises a band worn on the user's forehead.

17. The system of claim 1, wherein said means for attaching said matrix to a thermal sensitive organ of the blind person comprises a band worn on the user's forearm.

18. A system for providing images to a blind person having a thermal sensitive organ comprising:
    a receiver receiving an electronic signal corresponding to an optical image;
    a matrix receiving said electronic signal from said receiver, said matrix being formed of a plurality of thin film elements generating an infrared image corresponding to said video image; and
    a mounting member arranged and constructed to position said matrix with said thin film elements contacting said thermal sensitive organ so that the blind person perceives said optical image as said infrared image through his thermal sensitive organ;
    wherein said infrared image is generated by said matrix includes wavelengths of approximately 3.5, 7.0 and 11 microns in biophysics resonance with the tuned sensitivities, absorption spectra and the quantum vibrations, rotations and stretching in specific amino acids common to said organ, cortex and retina.

19. The system of claim 18 wherein each of said thin film elements generates an infrared element output in the infrared range, and wherein, in response to said electronic signal, the output of at least some of said thin film elements change to generate said infrared image.

20. A system for providing images to a blind person having a thermal sensitive organ comprising:
    a receiver receiving an electronic signal corresponding to an optical image;
    a matrix receiving said electronic signal from said receiver, said matrix being formed of a plurality of thin film elements selectively activated in accordance with said electronic signal to generate an infrared image corresponding to said optical image; and
    a mounting member arranged and constructed to position said matrix with said thin film elements contacting the thermal sensitive organ so that the blind person perceives said optical image as said infrared image through his thermal sensitive organ wherein said infrared image is generated by said matrix includes wavelengths of approximately 3.5, 7.0, and 11 microns in biophysics resonance with the tuned sensitivities, absorption spectra and the quantum vibrations, rotations and stretching in specific amino acids common to said organ, cortex and retina.

* * * * *